US009590196B2

(12) United States Patent
Strassner et al.

(10) Patent No.: US 9,590,196 B2
(45) Date of Patent: Mar. 7, 2017

(54) DINUCLEAR METAL COMPLEXES COMPRISING CARBENE LIGANDS AND THE USE THEREOF IN OLEDS

(71) Applicant: UDC Ireland Limited, Dublin (IE)

(72) Inventors: Thomas Strassner, Dresden (DE); Alexander Tronnier, Dresden (DE); Ute Heinemeyer, Neustadt (DE)

(73) Assignee: UDC Ireland Limited, Dublin (IE)

( * ) Notice: Subject to any disclaimer, the term of this patent is extended or adjusted under 35 U.S.C. 154(b) by 233 days.

(21) Appl. No.: 14/412,097

(22) PCT Filed: Jul. 17, 2013

(86) PCT No.: PCT/EP2013/065088
§ 371 (c)(1),
(2) Date: Dec. 30, 2014

(87) PCT Pub. No.: WO2014/012972
PCT Pub. Date: Jan. 23, 2014

(65) Prior Publication Data
US 2015/0171350 A1  Jun. 18, 2015

Related U.S. Application Data

(60) Provisional application No. 61/673,265, filed on Jul. 19, 2012.

(30) Foreign Application Priority Data

Jul. 19, 2012 (EP) ..................... 12177101

(51) Int. Cl.
*H01L 51/00* (2006.01)
*C07F 15/00* (2006.01)
*H01L 51/50* (2006.01)

(52) U.S. Cl.
CPC ........ *H01L 51/0087* (2013.01); *C07F 15/006* (2013.01); *C07F 15/0086* (2013.01); *H01L 51/5012* (2013.01)

(58) Field of Classification Search
CPC ............... C07F 15/006; C07F 15/0086; H01L 51/0087; H01L 51/5012
See application file for complete search history.

(56) References Cited

U.S. PATENT DOCUMENTS

| 2005/0196638 | A1* | 9/2005 | Son ................... H01L 51/5016 428/690 |
| 2007/0224446 | A1 | 9/2007 | Nakano et al. |
| 2009/0066226 | A1 | 3/2009 | Sugita et al. |
| 2009/0134784 | A1 | 5/2009 | Lin et al. |
| 2009/0153034 | A1 | 6/2009 | Lin et al. |
| 2009/0284138 | A1 | 11/2009 | Yasukawa et al. |
| 2009/0326236 | A1* | 12/2009 | Suh ....................... C07F 15/0033 548/103 |
| 2012/0199823 | A1* | 8/2012 | Molt ..................... C07F 15/0086 257/40 |

FOREIGN PATENT DOCUMENTS

| EP | 1 097 981 A2 | 5/2001 |
| EP | 1 786 050 A1 | 5/2007 |
| EP | 1 837 926 B1 | 5/2008 |
| EP | 1 970 371 A1 | 9/2008 |
| EP | 1 970 976 A1 | 9/2008 |
| EP | 1 988 587 A1 | 11/2008 |
| EP | 1 998 388 A1 | 12/2008 |
| EP | 2 034 538 A1 | 3/2009 |
| EP | 1 885 818 B1 | 1/2010 |
| EP | 2 180 029 A1 | 4/2010 |
| EP | 2 401 254 A1 | 1/2012 |
| JP | 2008-21687 A | 1/2008 |
| JP | 2008-66569 A | 3/2008 |
| JP | 2008-74939 A | 4/2008 |
| JP | 2008-84913 A | 4/2008 |
| JP | 2008-207520 A | 9/2008 |
| JP | 2009-21336 A | 1/2009 |
| JP | 2009-59767 A | 3/2009 |
| JP | 2009-114369 A | 5/2009 |
| JP | 2009-114370 A | 5/2009 |
| JP | 2009-135183 A | 6/2009 |
| JP | 2009-170764 A | 7/2009 |
| JP | 2009-182298 A | 8/2009 |
| JP | 2009-267255 A | 11/2009 |
| JP | 2010-21336 A | 1/2010 |

(Continued)

OTHER PUBLICATIONS

U.S. Appl. No. 14/416,103, filed Jan. 25, 2015, Strassner, et al.
International Search Report issued Oct. 10, 2013 in PCT/EP2013/065088.
Gurusamy Thangavelu Senthil Andavan, et al., "Synthesis and characterization of a free phenylene bis(N-heterocyclic carbene) and its di-Rh complex: Catalytic activity of the di-Rh and CCC-NHC Rh pincer complexes in intermolecular hydrosilylation of alkynes" Journal of Organometallic Chemistry, vol. 690, No. 24-25, XP027709194, Dec. 2005, pp. 5938-5947.

(Continued)

*Primary Examiner* — Alexander Kollias
(74) *Attorney, Agent, or Firm* — Riverside Law LLP

(57) ABSTRACT

The present invention relates to dinuclear metal-carbene complexes comprising a central atom selected from platinum and palladium, where both metal atoms are cyclometalated to the same aromatic group, to OLEDs (Organic Light-Emitting Diodes) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

14 Claims, No Drawings

(56) References Cited

FOREIGN PATENT DOCUMENTS

| | | |
|---|---|---|
| JP | 2010-40830 A | 2/2010 |
| JP | 2010-114180 A | 5/2010 |
| JP | 2010-135467 A | 6/2010 |
| WO | WO 00/32717 A1 | 6/2000 |
| WO | WO 00/70655 A2 | 11/2000 |
| WO | WO 2005/019373 A2 | 3/2005 |
| WO | WO 2005/113704 A2 | 12/2005 |
| WO | WO 2006/056418 A2 | 6/2006 |
| WO | WO 2006/128800 A1 | 12/2006 |
| WO | WO 2007/077810 A1 | 7/2007 |
| WO | WO 2007/108362 A1 | 9/2007 |
| WO | WO 2007/108459 A1 | 9/2007 |
| WO | WO 2007/114244 A1 | 10/2007 |
| WO | WO 2007/115970 A1 | 10/2007 |
| WO | WO 2007/115981 A1 | 10/2007 |
| WO | WO 2007/119816 A1 | 10/2007 |
| WO | WO 2008/000727 A1 | 1/2008 |
| WO | WO 2008/029652 A1 | 3/2008 |
| WO | WO 2008/029729 A1 | 3/2008 |
| WO | WO 2008/034758 A2 | 3/2008 |
| WO | WO 2008/035571 A1 | 3/2008 |
| WO | WO 2008/072596 A1 | 6/2008 |
| WO | WO 2008/090912 A1 | 7/2008 |
| WO | WO 2008/140114 A1 | 11/2008 |
| WO | WO 2008/146838 A1 | 12/2008 |
| WO | WO 2008/156105 A1 | 12/2008 |
| WO | WO 2009/003898 A1 | 1/2009 |
| WO | WO 2009/003919 A1 | 1/2009 |
| WO | WO 2009/008099 A1 | 1/2009 |
| WO | WO 2009/008100 A1 | 1/2009 |
| WO | WO 2009/046266 A1 | 4/2009 |
| WO | WO 2009/060742 A1 | 5/2009 |
| WO | WO 2009/060757 A1 | 5/2009 |
| WO | WO 2009/060779 A1 | 5/2009 |
| WO | WO 2009/060780 A1 | 5/2009 |
| WO | WO 2009/063757 A1 | 5/2009 |
| WO | WO 2009/084413 A1 | 7/2009 |
| WO | WO 2009/086028 A2 | 7/2009 |
| WO | WO 2009/104488 A1 | 8/2009 |
| WO | WO 2010/001830 A1 | 1/2010 |
| WO | WO 2010/004877 A1 | 1/2010 |
| WO | WO 2010/040777 A1 | 4/2010 |
| WO | WO 2010/044342 A1 | 4/2010 |
| WO | WO 2010/067746 A1 | 6/2010 |
| WO | WO 2010/079051 A1 | 7/2010 |
| WO | WO 2010/079678 A1 | 7/2010 |
| WO | WO 2010/087222 A1 | 8/2010 |
| WO | WO 2010/090077 A1 | 8/2010 |
| WO | WO 2010/095564 A1 | 8/2010 |
| WO | WO 2010/097433 | 9/2010 |
| WO | WO 2011/045337 A1 | 4/2011 |
| WO | WO 2011/073149 A1 | 6/2011 |
| WO | WO 2011/157779 A1 | 12/2011 |
| WO | WO 2011/157790 A1 | 12/2011 |

OTHER PUBLICATIONS

Laszlo Mercs, et al., "Probing Intermetallic Coupling in Dinuclear N-Heterocyclic Carbene Ruthenium(II) Complexes" Inorganic Chemistry, vol. 50, 2011, pp. 8188-8196.

Jan Kalinowski, et al., "Light-emitting devices based on organometallic platinum complexes as emitters" Coordination Chemistry Reviews, vol. 255, 2011, pp. 2401-2425.

* cited by examiner

DINUCLEAR METAL COMPLEXES COMPRISING CARBENE LIGANDS AND THE USE THEREOF IN OLEDS

The present invention relates to dinuclear metal-carbene complexes comprising a central atom selected from platinum and palladium, where both metal atoms are cyclometalated to the same aromatic group, to OLEDs (Organic Light-Emitting Diodes) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

OLEDs exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, smartphones, digital cameras, mp 3 players, laptops, etc. In addition, white OLEDs give great advantages over the illumination technologies known to date, especially a particularly high efficiency.

The prior art proposes numerous materials which emit light on excitation by electrical current.

WO2005/019373 discloses the use of transition metal complexes comprising at least one carbene ligand in OLEDs. According to WO2005/019373, a new compound class has been found which is suitable for electroluminescence in the blue, red and green region of the electromagnetic spectrum, which enables the production of full-color displays.

WO2006/056418 discloses the use of transition metal-carbene complexes having at least one unsymmetrically substituted carbene ligand in organic light-emitting diodes. The transition metal-carbene complexes are suitable for electroluminescence in the blue, red and green region of the electromagnetic spectrum.

WO2005/113704 discloses numerous different types of carbene ligands with various transition metal centers, including Pt.

WO2009/046266 discloses complexes with tridentate ligands having two carbene moieties, The disclosed complexes do not include dinuclear complexes where both metal centers are cyclometalated to the same aromatic group.

WO2011/045337 discloses dinuclear Pt complexes having carbene ligands:

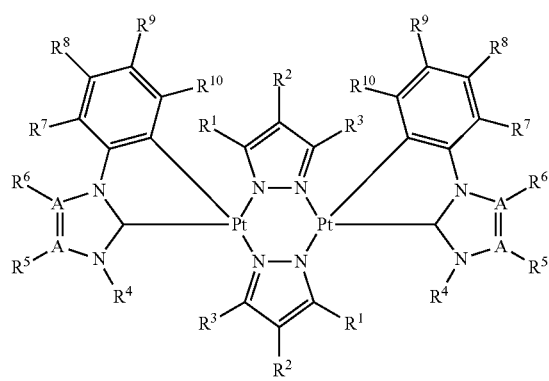

(Ia)

or

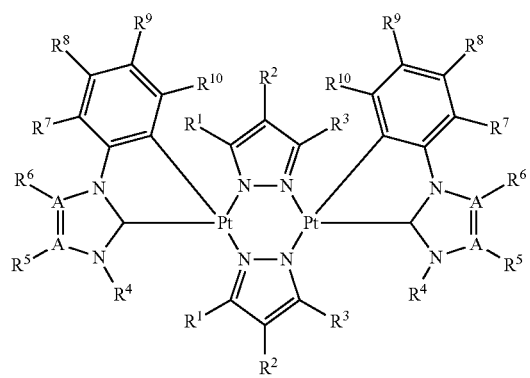

(Ib)

The bridging unit does not form part of the carbene ligands.

WO2011/073149 discloses Pt complexes having carbene ligands and acetylacetonato derived ligands. However, no binuclear complexes are included there.

In Inorg. Chem. 2011, 50, 8188 Albrecht et al. report a binuclear Ru complex with both metal atoms cyclometalated to the same aromatic group:

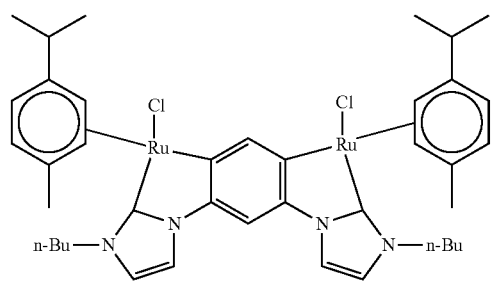

Solutions of the binuclear Ru complex in CDCl$_3$ were unstable. A gradual transformation to a structurally strongly related complex was noted (t½=20 h) and eventual decomposition (within ca. 40 h), as deduced from the accumulation of free cymene. According to the authors the limited stability of the phenylene-bridged binuclear Ru complex renders it unsuitable for electronic applications.

Jan Kalinowski et al., Coord. Chem. Rev. 2011, 255, 2401 describes one major challenge of luminescent Pt complexes, which is the strong dependency of the color on the concentration of the material. In particular this can be a problem in terms of reproducibility.

Even though there are already known Pd and Pt carbene complexes which are suitable for use in OLEDs, especially as light-emitting substances, it is desirable to provide more stable and/or more efficient compounds which are usable in industry.

It is therefore an object of the present invention to provide palladium and platinum complexes which are suitable for use in organic electronic components. More particularly, the palladium and platinum complexes shall be suitable for use in OLEDs as emitters, matrix material, charge transport material, or charge blockers. The complexes shall be particularly suitable for color-tuning of the electroluminescence, which enables, for example, the production of full-color displays and white OLEDs. It is a further object of the present invention to provide corresponding complexes which can be used as a mixture with a host compound (matrix material) or as a pure layer as a light-emitting layer in OLEDs. More particularly, it is desirable to provide Pd and Pt transition metal complexes which exhibit a spectrum of properties improved over known Pd or Pt complexes, for example improved efficiencies, improved CIE color coordinates, decreased color dependency on the emitter doping concentration and/or improved lifetime/stability.

Surprisingly, it was found that these objects are achieved in accordance with the invention by metal-carbene complexes of the general formula

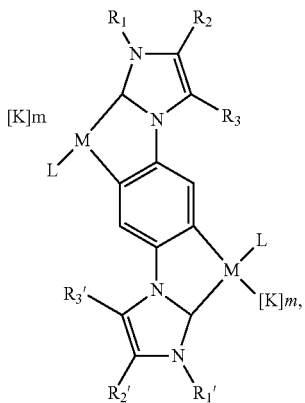

(I)

or

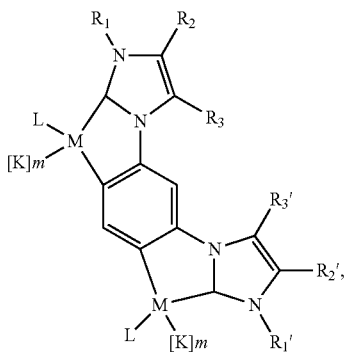

(II)

wherein
M is Pd or Pt,
m is an integer selected from 0 or 1,
$R_1$ and $R_1'$ are each independently a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms;

$R_2$, $R_2'$, $R_3$ and $R_3'$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, or a group with donor or acceptor action, or $R_1$ and $R_2$ and/or $R_1'$ and $R_2'$ together with the atoms to which they are bonded form an optionally substituted, saturated or unsaturated or aromatic ring optionally interrupted by at least one further heteroatom and having a total of 5 to 18 carbon atoms and/or heteroatoms, and may optionally be fused to at least one further optionally substituted saturated or unsaturated or aromatic ring optionally interrupted by at least one further heteroatom and having a total of 5 to 18 carbon atoms and/or heteroatoms;

K is a neutral monodentate ligand, and
L is a monoanionic ligand, which can be mono- or bidentate.

The inventive dinuclear metal-carbene complexes, comprising a central metal atom selected from platinum and palladium, are characterized in that both metal atoms are cyclometalated to the same aromatic group.

The inventive dinuclear metal-carbene complexes can be used in electronic devices, especially OLEDs, for example, as emitter, matrix material, charge transport material and/or charge or exciton blocker.

The inventive dinuclear metal-carbene complexes are generally notable for light emission in a wide range of the electromagnetic spectrum.

The inventive dinuclear metal-carbene complexes are therefore suitable with particular preference as emitter material in OLEDs.

M is Pd or Pt, preferably Pt.

In one preferred embodiment of the present invention $R_2$ and $R_2'$ are H. In one preferred embodiment of the present invention $R_3$ and $R_3'$ are H. In a more preferred embodiment $R_2$, $R_2'$, $R_3$ and $R_3'$ are H.

A bidentate ligand is understood to mean a ligand coordinated at two sites to the transition metal atom M. A monodentate ligand is understood to mean a ligand coordinated at one site on the ligand to the transition metal atom M.

Suitable uncharged mono- or bidentate ligands K are preferably selected from the group consisting of phosphines, both mono- and bisphosphines; phosphonates, both mono- and bisphosphonates, and derivatives thereof, arsenates, both mono- and bisarsenates, and derivatives thereof; phosphites, both mono- and bisphosphites; CO; pyridines, both mono- and bispyridines; nitriles, dinitriles, allyl, diimines, nonconjugated dienes and conjugated dienes which form a π complex with M. Particularly preferred uncharged mono- or bidentate ligands K are selected from the group consisting of phosphines, both mono- and bisphosphines, preferably trialkyl-, triaryl- or alkylarylphosphines, more preferably $PAr_3$ where Ar is a substituted or unsubstituted aryl radical and the three aryl radicals in $PAr_3$ may be the same or different, more preferably $PPh_3$, $PEt_3$, $PnBu_3$, $PEt_2Ph$, $PMe_2Ph$, $PnBu_2Ph$; phosphonates and derivatives thereof, arsenates and derivatives thereof, phosphites, CO; pyridines, both mono- and bispyridines, where the pyridines may be substituted by alkyl or aryl groups; nitriles and dienes which form a π complex with $M^1$, preferably $\eta^4$-diphenyl-1,3-butadiene, $\eta^4$-1,3-pentadiene, $\eta^4$-1-phenyl-1,3-pentadiene, $\eta^4$-1,4-dibenzyl-1,3-butadiene, $\eta^4$-2,4-hexadiene, $\eta^4$-3-methyl-1,3-pentadiene, $\eta^4$-1,4-ditolyl-1,3-butadiene, $\eta^4$-1,4-bis(trimethylsilyl)-1,3-butadiene and $\eta^2$- or $\eta^4$-cyclooctadiene (each 1,3 and each 1,5), more preferably 1,4-diphenyl-1,3-butadiene, 1-phenyl-1,3-pentadiene, 2,4-hexadiene, butadiene, $\eta^2$-cyclooctene, $\eta^4$-1,3-cyclooctadiene and $\eta^4$-1,5-cyclooctadiene. Very particularly preferred uncharged monodentate ligands are selected from the group consisting of $PPh_3$, $P(OPh)_3$, $AsPh_3$, CO, pyridine, nitriles and derivatives thereof. Suitable uncharged mono- or bidentate ligands are preferably 1,4-diphenyl-1,3-butadiene, 1-phenyl-1,3-pentadiene, 2,4-hexadiene, $\eta^4$-cyclooctadiene and $\eta^2$-cyclooctadiene (each 1,3 and each 1,5).

Suitable mono- or dianionic ligands L, preferably monoanionic ligands L which may be mono- or bidentate, are the ligands typically used as mono- or bidentate mono- or dianionic ligands.

Suitable monoanionic monodentate ligands are, for example, halides, especially $Cl^-$ and $Br^-$, pseudohalides, especially $CN^-$, cyclopentadienyl ($Cp^-$), hydride, alkyl radicals joined to the transition metal M via a sigma bond, for example $CH_3$, alkylaryl radicals joined to the transition metal M via a sigma bond, for example benzyl.

Preferably m is 0 and L is a monoanionic bidentate ligand.

In a preferred embodiment of the present invention L is selected from the group consisting of picolinato, salicylato, 8-hydroxyquinolato, or ligands of the formula (A)

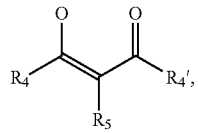

(A)

in which $R_4$ and $R_4'$ are in each case independently a linear or branched alkyl radical having 1 to 6 carbons atoms optionally bearing at least one functional group; substituted or unsubstituted cycloalkyl radical having 3 to 20 carbon atoms, substituted or unsubstituted aryl radical having 6 to 20 carbon atoms, preferably unsubstituted phenyl, 2,6-dialkylphenyl or 2,4,6-trialkylphenyl; substituted or unsubstituted heteroaryl radical having a total of 5 to 18 carbon atoms and/or heteroatoms, and $R_5$ is hydrogen, a linear or branched alkyl radical having 1 to 6 carbon atoms, substituted or unsubstituted aryl radical having 6 to 20 carbon atoms.

The alkyl radical having 1 to 6 carbons atoms $R_4$ and $R_4'$ is preferably selected from methyl, trifluoromethyl, ethyl, isopropyl, tert-butyl. The aryl radical having 6 to 20 carbon atoms is preferably selected from unsubstituted phenyl, 2,6-dialkylphenyl and 2,4,6-trialkylphenyl. The cycloalkyl radical having 3 to 20 carbon atoms $R_4$ and $R_4'$ is preferably selected from cyclopentyl and cyclohexyl. The heteroaryl radical having a total of 5 to 18 carbon atoms and/or heteroatoms $R_4$ and $R_4'$ is preferably selected from thienyl, or furanyl.

Examples of particularly suitable compounds $HL$,

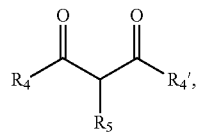

from which the ligands L are derived, include

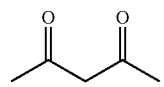

(2,4-pentanedione[acac])

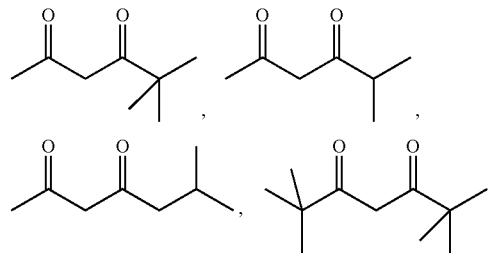

(2,2,6,6-tetramethyl-3,5-heptanedione[TMH])

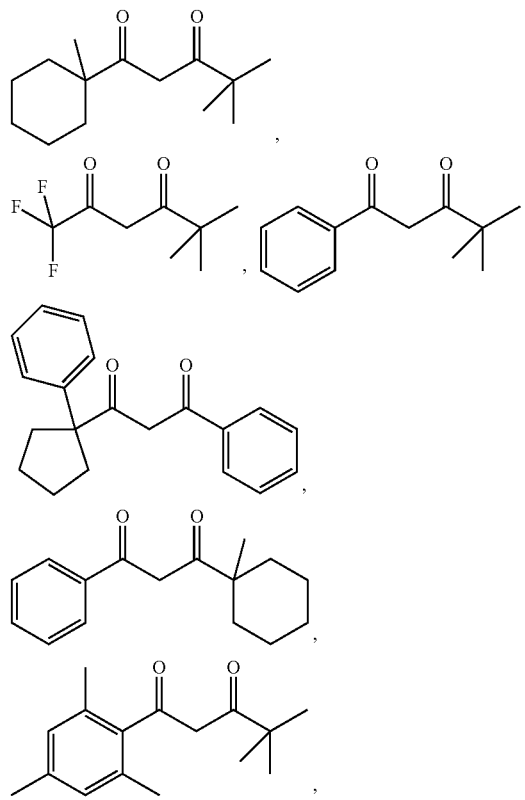

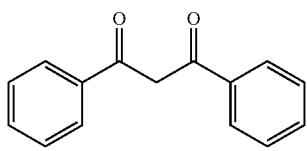

(1,3-diphenyl-1,3-propanedione[DI]),

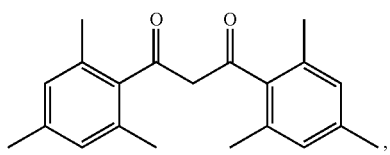

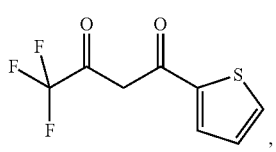

(4,4,4-trifluoro-1-(2-thienyl)-1,3-butanedione[TTFA])

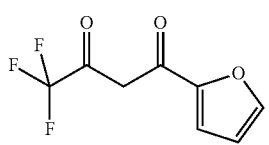

(7,7-dimethyl-1,1,1,2,2,3,3-heptafluoro-4,6-octanedione [FOD]),

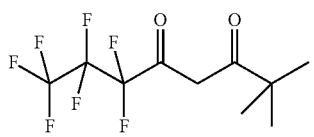 [SMILES: CC(C)(C)C(=O)CC(=O)C(F)(F)C(F)(F)C(F)(F)F]

(1,1,1,5,5,5-hexafluoro-2,4-pentanedione[F6acac]),

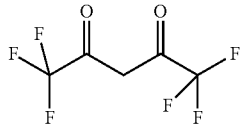

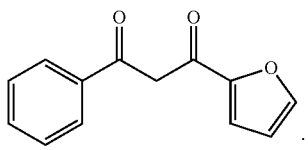

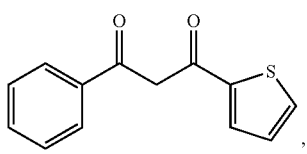

and

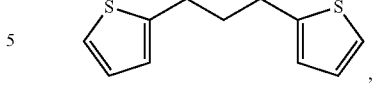

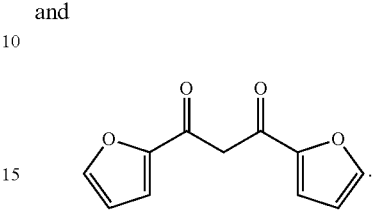

In a particularly preferred embodiment of the present invention L is selected from ligands of the formula (A), in which $R_4$ and $R_4$ are methyl, ethyl, isopropyl, tert-butyl; phenyl, 2,6-dialkylphenyl or 2,4,6-trialkylphenyl; and $R_5$ is hydrogen.

In a preferred embodiment the present invention is directed to metal-carbene complexes of (III)

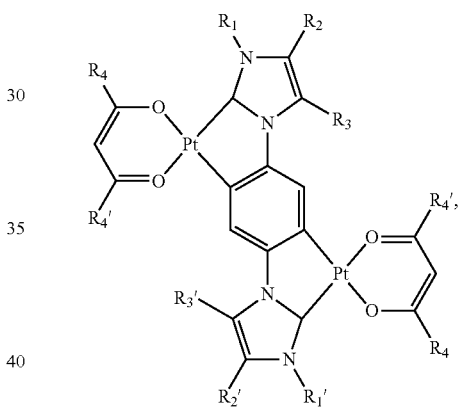

the general formula or (IV)

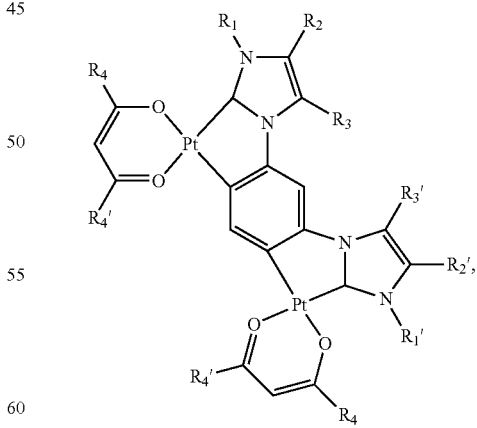

wherein
$R_1$ and $R_1'$ are each independently a linear or branched alkyl radical having 1 to 6 carbon atoms, substituted or unsubstituted cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms,
$R_2$, $R_2'$, $R_3$ and $R_3'$ are each independently hydrogen, a linear or branched alkyl radical having 1 to 6 carbon atoms, substituted or unsubstituted cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, or a group with donor or acceptor action selected from halogen radicals, preferably F, Cl, more preferably F; $CF_3$, CN and $SiMe_3$; or $R_1$ and $R_2$ and/or $R_1'$ and $R_2'$ form, together with the atoms to which they are bonded, an optionally substituted unsaturated, saturated or aromatic ring which is optionally interrupted by at least one further heteroatom, has a total of 5 to 18 carbon atoms and/or heteroatoms and may optionally be fused to at least one further optionally substituted saturated or unsaturated or aromatic ring optionally interrupted by at least one further heteroatom and having a total of 5 to 18 carbon atoms and/or heteroatoms, $R_4$ and $R_4'$ are in each case independently a linear or branched alkyl radical having 1 to 6 carbons atoms, preferably methyl, ethyl, isopropyl, tert-butyl; substituted or unsubstituted aryl radical having 6 to 20 carbon atoms, preferably unsubstituted phenyl, 2,6-dialkylphenyl or 2,4,6-trialkylphenyl; substituted or unsubstituted heteroaryl radical having a total of 5 to 18 carbon atoms and/or heteroatoms.

$R_1$ is preferably a linear or branched alkyl radical having 1 to 6 carbon atoms, substituted or unsubstituted cycloalkyl radical having 3 to 12 carbon atoms, substituted or unsubstituted aryl radical having 6 to 15 carbon atoms. More preferably, $R_1$ is $C_1$-$C_6$alkyl, phenyl, or

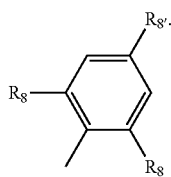

$R_2$ and $R_3$ are preferably each independently hydrogen, a linear or branched alkyl radical having 1 to 6 carbon atoms, substituted or unsubstituted aryl radical having 6 to 18 carbon atoms, group with donor or acceptor action selected from halogen radicals, preferably F, Cl, more preferably F; $CF_3$, CN and $SiMe_3$. More preferably, $R_2$ and $R_3$ are each independently hydrogen, a linear or branched alkyl radical having 1 to 6 carbon atoms, or

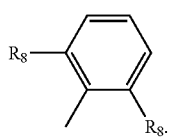

Alternatively, $R_1$ and $R_2$ form, together with the atoms to which they are bonded, an optionally substituted unsaturated, saturated or aromatic ring which is optionally interrupted by at least one further heteroatom, has a total of 5 to 18 carbon atoms and/or heteroatoms. Preferably, $R_1$ and $R_2$ form, together with the atoms to which they are bonded, a ring

$R_4$ and $R_4'$ are preferably in each case independently a linear or branched alkyl radical having 1 to 6 carbons atoms, preferably methyl, ethyl, isopropyl, tert-butyl; substituted or unsubstituted aryl radical having 6 to 15 carbon atoms, preferably unsubstituted phenyl, 2,6-dialkylphenyl or 2,4,6-trialkylphenyl. More preferably, $R_4$ and $R_{4'}$ are each independently a linear or branched alkyl radical having 1 to 6 carbon atoms, phenyl, or

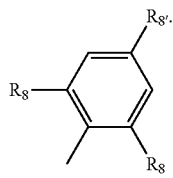

$R_8$ is a linear or branched alkyl radical having 1 to 6 carbon atoms and $R_{8'}$ is H, or a linear or branched alkyl radical having 1 to 6 carbon atoms.

In said embodiment metal-carbene complexes of the general formula

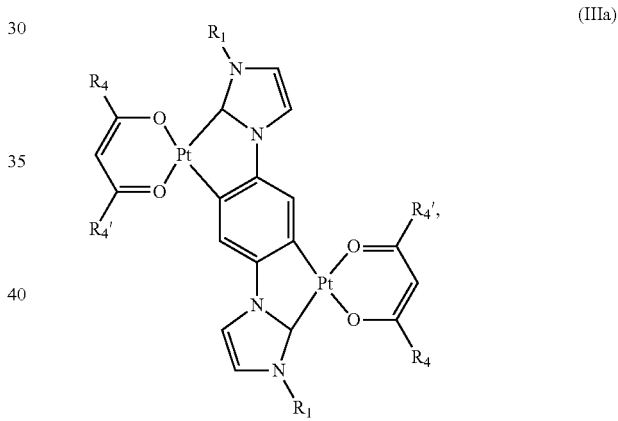

(IIIa)

or (IVa)

are more preferred, wherein
R₁ is a linear or branched alkyl radical having 1 to 6 carbon atoms, preferably methyl, ethyl, isopropyl, tert-butyl; and R₄ and R₄' are in each case independently a linear or branched alkyl radical having 1 to 6 carbons atoms, preferably methyl, ethyl, isopropyl, tert-butyl; substituted or unsubstituted aryl radical having 6 to 15 carbon atoms, preferably unsubstituted phenyl, 2,6-dialkylphenyl or 2,4,6-trialkylphenyl, such as, for example, phenyl, or

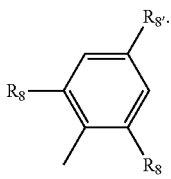

R₈ is a linear or branched alkyl radical having 1 to 6 carbon atoms and R₈' is H, or a linear or branched alkyl radical having 1 to 6 carbon atoms. A linear or branched alkyl radical having 1 to 6 carbon atoms is, for example, methyl, ethyl, propyl, iso-propyl, butyl, tert-butyl, pentyl, or hexyl; preferably methyl, ethyl, isopropyl, tert-butyl.

In another preferred embodiment the present invention is directed to metal-carbene complexes of the general formula

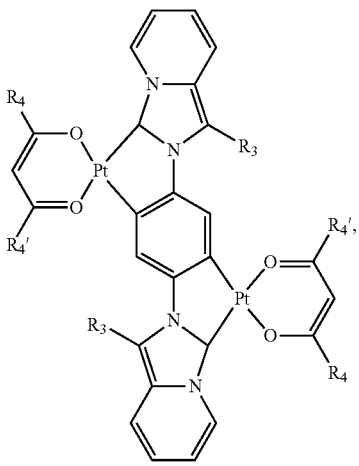

(IIIb)

R₃ is H, and R₄ and R₄' are in each case independently a linear or branched alkyl radical having 1 to 6 carbons atoms, preferably methyl, ethyl, isopropyl, tert-butyl; substituted or unsubstituted aryl radical having 6 to 15 carbon atoms, preferably unsubstituted phenyl, 2,6-dialkylphenyl or 2,4,6-trialkylphenyl, such as, for example, phenyl or

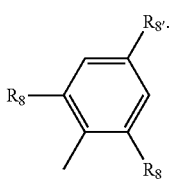

R₈ is a linear or branched alkyl radical having 1 to 6 carbon atoms and R₈' is H, or a linear or branched alkyl radical having 1 to 6 carbon atoms.

A linear or branched alkyl radical having 1 to 6 carbon atoms is, for example, methyl, ethyl, propyl, iso-propyl, butyl, tert-butyl, pentyl, or hexyl; preferably methyl, ethyl, isopropyl, tert-butyl.

Examples of suitable compounds are shown in the tables below:

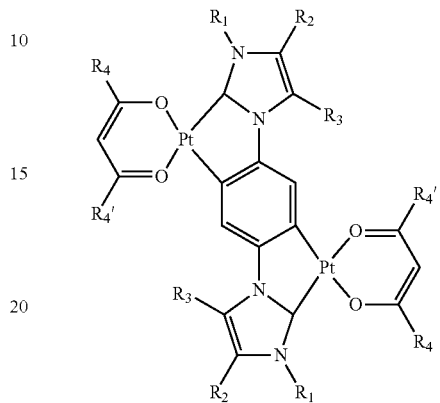

| Cpd. | R₁ | R₂ | R₃ | R₄, R₄' |
|---|---|---|---|---|
| D-1 | CH₃ | H | H | Me |
| D-2 | CH₃ | H | H | t-Bu |
| D-3 | CH₃ | H | H | Ph |
| D-4 | CH₃ | H | H | TMP |
| D-5 | CH₃ | H | H | TIPP |
| D-6 | CH₃ | H | H | DMP |
| D-7 | CH₃ | H | H | DIPP |
| D-8 | iPr | H | H | Me |
| D-9 | iPr | H | H | t-Bu |
| D-10 | iPr | H | H | Ph |
| D-11 | iPr | H | H | TMP |
| D-12 | iPr | H | H | TIPP |
| D-13 | iPr | H | H | DMP |
| D-14 | iPr | H | H | DIPP |
| D-15 | TMP | H | H | Me |
| D-16 | TMP | H | H | t-Bu |
| D-17 | TMP | H | H | Ph |
| D-18 | TMP | H | H | TMP |
| D-19 | TMP | H | H | TIPP |
| D-20 | TMP | H | H | DMP |
| D-21 | TMP | H | H | DIPP |
| D-22 | Ph | H | H | Me |
| D-23 | Ph | H | H | t-Bu |
| D-24 | Ph | H | H | Ph |
| D-25 | Ph | H | H | TMP |
| D-26 | Ph | H | H | TIPP |
| D-27 | Ph | H | H | DMP |
| D-28 | Ph | H | H | DIPP |
| D-29 | CH₃ | tBu | H | Me |
| D-30 | CH₃ | tBu | H | t-Bu |
| D-31 | CH₃ | tBu | H | Ph |
| D-32 | CH₃ | tBu | H | TMP |
| D-33 | CH₃ | tBu | H | TIPP |
| D-34 | CH₃ | tBu | H | DMP |
| D-35 | CH₃ | tBu | H | DIPP |
| D-36 | iPr | tBu | H | Me |
| D-37 | iPr | tBu | H | t-Bu |
| D-38 | iPr | tBu | H | Ph |
| D-39 | iPr | tBu | H | TMP |
| D-40 | iPr | tBu | H | TIPP |
| D-41 | iPr | tBu | H | DMP |
| D-42 | iPr | tBu | H | DIPP |
| D-43 | TMP | tBu | H | Me |
| D-44 | TMP | tBu | H | t-Bu |
| D-45 | TMP | tBu | H | Ph |
| D-46 | TMP | tBu | H | TMP |
| D-47 | TMP | tBu | H | TIPP |

-continued

| Cpd. | R₁ | R₂ | R₃ | R₄, R₄' |
|---|---|---|---|---|
| D-48 | TMP | tBu | H | DMP |
| D-49 | TMP | tBu | H | DIPP |
| D-50 | Ph | tBu | H | Me |
| D-51 | Ph | tBu | H | t-Bu |
| D-52 | Ph | tBu | H | Ph |
| D-53 | Ph | tBu | H | TMP |
| D-55 | Ph | tBu | H | TIPP |
| D-56 | Ph | tBu | H | DMP |
| D-57 | Ph | tBu | H | DIPP |
| D-58 | CH₃ | iBu | H | Me |
| D-59 | CH₃ | iBu | H | t-Bu |
| D-60 | CH₃ | iBu | H | Ph |
| D-61 | CH₃ | iBu | H | TMP |
| D-62 | CH₃ | iBu | H | TIPP |
| D-63 | CH₃ | iBu | H | DMP |
| D-64 | CH₃ | iBu | H | DIPP |
| D-65 | iPr | iBu | H | Me |
| D-66 | iPr | iBu | H | t-Bu |
| D-67 | iPr | iBu | H | Ph |
| D-68 | iPr | iBu | H | TMP |
| D-69 | iPr | iBu | H | TIPP |
| D-70 | iPr | iBu | H | DMP |
| D-71 | iPr | iBu | H | DIPP |
| D-72 | TMP | iBu | H | Me |
| D-73 | TMP | iBu | H | t-Bu |
| D-74 | TMP | iBu | H | Ph |
| D-75 | TMP | iBu | H | TMP |
| D-76 | TMP | iBu | H | TIPP |
| D-77 | TMP | iBu | H | DMP |
| D-78 | TMP | iBu | H | DIPP |
| D-79 | Ph | iBu | H | Me |
| D-80 | Ph | iBu | H | t-Bu |
| D-81 | Ph | iBu | H | Ph |
| D-82 | Ph | iBu | H | TMP |
| D-83 | Ph | iBu | H | TIPP |
| D-84 | Ph | iBu | H | DMP |
| D-85 | Ph | iBu | H | DIPP |
| D-86 | CH₃ | H | iBu | Me |
| D-87 | CH₃ | H | iBu | t-Bu |
| D-88 | CH₃ | H | iBu | Ph |
| D-89 | CH₃ | H | iBu | TMP |
| D-90 | CH₃ | H | iBu | TIPP |
| D-91 | CH₃ | H | iBu | DMP |
| D-92 | CH₃ | H | iBu | DIPP |
| D-93 | iPr | H | iBu | Me |
| D-94 | iPr | H | iBu | t-Bu |
| D-95 | iPr | H | iBu | Ph |
| D-96 | iPr | H | iBu | TMP |
| D-97 | iPr | H | iBu | TIPP |
| D-98 | iPr | H | iBu | DMP |
| D-99 | iPr | H | iBu | DIPP |
| D-100 | TMP | H | iBu | Me |
| D-101 | TMP | H | iBu | t-Bu |
| D-102 | TMP | H | iBu | Ph |
| D-103 | TMP | H | iBu | TMP |
| D-104 | TMP | H | iBu | TIPP |
| D-105 | TMP | H | iBu | DMP |
| D-106 | TMP | H | iBu | DIPP |
| D-107 | Ph | H | iBu | Me |
| D-108 | Ph | H | iBu | t-Bu |
| D-109 | Ph | H | iBu | Ph |
| D-110 | Ph | H | iBu | TMP |
| D-111 | Ph | H | iBu | TIPP |
| D-112 | Ph | H | iBu | DMP |
| D-113 | Ph | H | iBu | DIPP |
| D-114 | CH₃ | DIPP | H | Me |
| D-115 | CH₃ | DIPP | H | t-Bu |
| D-116 | CH₃ | DIPP | H | Ph |
| D-117 | CH₃ | DIPP | H | TMP |
| D-118 | CH₃ | DIPP | H | TIPP |
| D-119 | CH₃ | DIPP | H | DMP |
| D-120 | CH₃ | DIPP | H | DIPP |
| D-121 | iPr | DIPP | H | Me |
| D-122 | iPr | DIPP | H | t-Bu |
| D-123 | iPr | DIPP | H | Ph |
| D-124 | iPr | DIPP | H | TMP |
| D-125 | iPr | DIPP | H | TIPP |

-continued

| Cpd. | R₁ | R₂ | R₃ | R₄, R₄' |
|---|---|---|---|---|
| D-126 | iPr | DIPP | H | DMP |
| D-127 | iPr | DIPP | H | DIPP |
| D-128 | TMP | DIPP | H | Me |
| D-129 | TMP | DIPP | H | t-Bu |
| D-130 | TMP | DIPP | H | Ph |
| D-131 | TMP | DIPP | H | TMP |
| D-132 | TMP | DIPP | H | TIPP |
| D-133 | TMP | DIPP | H | DMP |
| D-134 | TMP | DIPP | H | DIPP |
| D-135 | Ph | DIPP | H | Me |
| D-136 | Ph | DIPP | H | t-Bu |
| D-137 | Ph | DIPP | H | Ph |
| D-138 | Ph | DIPP | H | TMP |
| D-139 | Ph | DIPP | H | TIPP |
| D-140 | Ph | DIPP | H | DMP |
| D-141 | Ph | DIPP | H | DIPP |
| D-142 | CH₃ | H | DMP | Me |
| D-143 | CH₃ | H | DMP | t-Bu |
| D-144 | CH₃ | H | DMP | Ph |
| D-145 | CH₃ | H | DMP | TMP |
| D-146 | CH₃ | H | DMP | TIPP |
| D-147 | CH₃ | H | DMP | DMP |
| D-148 | CH₃ | H | DMP | DIPP |
| D-149 | iPr | H | DMP | Me |
| D-150 | iPr | H | DMP | t-Bu |
| D-151 | iPr | H | DMP | Ph |
| D-152 | iPr | H | DMP | TMP |
| D-153 | iPr | H | DMP | TIPP |
| D-154 | iPr | H | DMP | DMP |
| D-155 | iPr | H | DMP | DIPP |
| D-156 | TMP | H | DMP | Me |
| D-157 | TMP | H | DMP | t-Bu |
| D-158 | TMP | H | DMP | Ph |
| D-159 | TMP | H | DMP | TMP |
| D-160 | TMP | H | DMP | TIPP |
| D-161 | TMP | H | DMP | DMP |
| D-162 | TMP | H | DMP | DIPP |
| D-163 | Ph | H | DMP | Me |
| D-164 | Ph | H | DMP | t-Bu |
| D-165 | Ph | H | DMP | Ph |
| D-166 | Ph | H | DMP | TMP |
| D-167 | Ph | H | DMP | TIPP |
| D-168 | Ph | H | DMP | DMP |
| D-169 | Ph | H | DMP | DIPP |

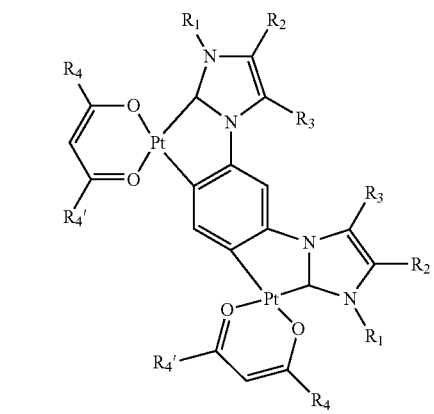

| Cpd. | R₁ | R₂ | R₃ | R₄, R₄' |
|---|---|---|---|---|
| E-1 | CH₃ | H | H | Me |
| E-2 | CH₃ | H | H | t-Bu |
| E-3 | CH₃ | H | H | Ph |
| E-4 | CH₃ | H | H | TMP |

-continued

| Cpd. | $R_1$ | $R_2$ | $R_3$ | $R_4, R_4'$ |
|---|---|---|---|---|
| E-5 | $CH_3$ | H | H | TIPP |
| E-6 | $CH_3$ | H | H | DMP |
| E-7 | $CH_3$ | H | H | DIPP |
| E-8 | iPr | H | H | Me |
| E-9 | iPr | H | H | t-Bu |
| E-10 | iPr | H | H | Ph |
| E-11 | iPr | H | H | TMP |
| E-12 | iPr | H | H | TIPP |
| E-13 | iPr | H | H | DMP |
| E-14 | iPr | H | H | DIPP |
| E-15 | TMP | H | H | Me |
| E-16 | TMP | H | H | t-Bu |
| E-17 | TMP | H | H | Ph |
| E-18 | TMP | H | H | TMP |
| E-19 | TMP | H | H | TIPP |
| E-20 | TMP | H | H | DMP |
| E-21 | TMP | H | H | DIPP |
| E-22 | Ph | H | H | Me |
| E-23 | Ph | H | H | t-Bu |
| E-24 | Ph | H | H | Ph |
| E-25 | Ph | H | H | TMP |
| E-26 | Ph | H | H | TIPP |
| E-27 | Ph | H | H | DMP |
| E-28 | Ph | H | H | DIPP |
| E-29 | $CH_3$ | tBu | H | Me |
| E-30 | $CH_3$ | tBu | H | t-Bu |
| E-31 | $CH_3$ | tBu | H | Ph |
| E-32 | $CH_3$ | tBu | H | TMP |
| E-33 | $CH_3$ | tBu | H | TIPP |
| E-34 | $CH_3$ | tBu | H | DMP |
| E-35 | $CH_3$ | tBu | H | DIPP |
| E-36 | iPr | tBu | H | Me |
| E-37 | iPr | tBu | H | t-Bu |
| E-38 | iPr | tBu | H | Ph |
| E-39 | iPr | tBu | H | TMP |
| E-40 | iPr | tBu | H | TIPP |
| E-41 | iPr | tBu | H | DMP |
| E-42 | iPr | tBu | H | DIPP |
| E-43 | TMP | tBu | H | Me |
| E-44 | TMP | tBu | H | t-Bu |
| E-45 | TMP | tBu | H | Ph |
| E-46 | TMP | tBu | H | TMP |
| E-47 | TMP | tBu | H | TIPP |
| E-48 | TMP | tBu | H | DMP |
| E-49 | TMP | tBu | H | DIPP |
| E-50 | Ph | tBu | H | Me |
| E-51 | Ph | tBu | H | t-Bu |
| E-52 | Ph | tBu | H | Ph |
| E-53 | Ph | tBu | H | TMP |
| E-55 | Ph | tBu | H | TIPP |
| E-56 | Ph | tBu | H | DMP |
| E-57 | Ph | tBu | H | DIPP |
| E-58 | $CH_3$ | iBu | H | Me |
| E-59 | $CH_3$ | iBu | H | t-Bu |
| E-60 | $CH_3$ | iBu | H | Ph |
| E-61 | $CH_3$ | iBu | H | TMP |
| E-62 | $CH_3$ | iBu | H | TIPP |
| E-63 | $CH_3$ | iBu | H | DMP |
| E-64 | $CH_3$ | iBu | H | DIPP |
| E-65 | iPr | iBu | H | Me |
| E-66 | iPr | iBu | H | t-Bu |
| E-67 | iPr | iBu | H | Ph |
| E-68 | iPr | iBu | H | TMP |
| E-69 | iPr | iBu | H | TIPP |
| E-70 | iPr | iBu | H | DMP |
| E-71 | iPr | iBu | H | DIPP |
| E-72 | TMP | iBu | H | Me |
| E-73 | TMP | iBu | H | t-Bu |
| E-74 | TMP | iBu | H | Ph |
| E-75 | TMP | iBu | H | TMP |
| E-76 | TMP | iBu | H | TIPP |
| E-77 | TMP | iBu | H | DMP |
| E-78 | TMP | iBu | H | DIPP |
| E-79 | Ph | iBu | H | Me |
| E-80 | Ph | iBu | H | t-Bu |
| E-81 | Ph | iBu | H | Ph |
| E-82 | Ph | iBu | H | TMP |

-continued

| Cpd. | $R_1$ | $R_2$ | $R_3$ | $R_4, R_4'$ |
|---|---|---|---|---|
| E-83 | Ph | iBu | H | TIPP |
| E-84 | Ph | iBu | H | DMP |
| E-85 | Ph | iBu | H | DIPP |
| E-86 | $CH_3$ | DIPP | H | Me |
| E-87 | $CH_3$ | DIPP | H | t-Bu |
| E-88 | $CH_3$ | DIPP | H | Ph |
| E-89 | $CH_3$ | DIPP | H | TMP |
| E-90 | $CH_3$ | DIPP | H | TIPP |
| E-91 | $CH_3$ | DIPP | H | DMP |
| E-92 | $CH_3$ | DIPP | H | DIPP |
| E-93 | iPr | DIPP | H | Me |
| E-94 | iPr | DIPP | H | t-Bu |
| E-95 | iPr | DIPP | H | Ph |
| E-96 | iPr | DIPP | H | TMP |
| E-97 | iPr | DIPP | H | TIPP |
| E-98 | iPr | DIPP | H | DMP |
| E-99 | iPr | DIPP | H | DIPP |
| E-100 | TMP | DIPP | H | Me |
| E-101 | TMP | DIPP | H | t-Bu |
| E-102 | TMP | DIPP | H | Ph |
| E-103 | TMP | DIPP | H | TMP |
| E-104 | TMP | DIPP | H | TIPP |
| E-105 | TMP | DIPP | H | DMP |
| E-106 | TMP | DIPP | H | DIPP |
| E-107 | Ph | DIPP | H | Me |
| E-108 | Ph | DIPP | H | t-Bu |
| E-109 | Ph | DIPP | H | Ph |
| E-110 | Ph | DIPP | H | TMP |
| E-111 | Ph | DIPP | H | TIPP |
| E-112 | Ph | DIPP | H | DMP |
| E-113 | Ph | DIPP | H | DIPP |

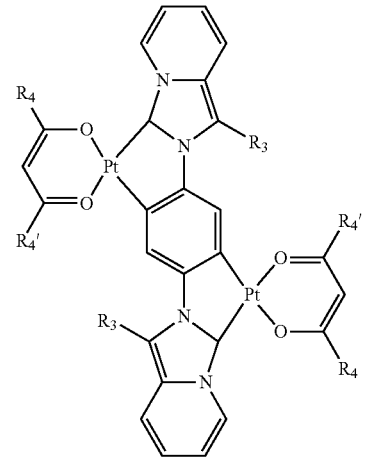

| Cpd. | $R_3$ | $R_4, R_4'$ |
|---|---|---|
| F-1 | H | Me |
| F-2 | H | t-Bu |
| F-3 | H | Ph |
| F-4 | H | TMP |
| F-5 | H | TIPP |
| F-6 | H | DMP |
| F-7 | H | DIPP |
| F-8 | iPr | Me |
| F-9 | iPr | t-Bu |
| F-10 | iPr | Ph |
| F-11 | iPr | TMP |
| F-12 | iPr | TIPP |
| F-13 | iPr | DMP |
| F-14 | iPr | DIPP |

-continued

| Cpd. | R₃ | R₄, R₄' |
|---|---|---|
| F-15 | DIPP | Me |
| F-16 | DIPP | t-Bu |
| F-17 | DIPP | Ph |
| F-18 | DIPP | TMP |
| F-19 | DIPP | TIPP |
| F-20 | DIPP | DMP |
| F-21 | DIPP | DIPP |
| F-22 | Me | t-Bu |
| F-23 | Et | t-Bu |
| F-24 | i-Bu | t-Bu |
| F-25 | t-Bu | t-Bu |
| F-26 | DMP | t-Bu |
| F-27 | TIPP | t-Bu |
| F-28 | TMP | t-Bu |

[DIPP = 2,6-Diisopropylphenyl, TIPP = 2,4,6-Triisopropylphenyl, DMP = 2,6-Dimethylphenyl, TMP = 2,4,6-Trimethylphenyl]

A process for preparing the dinuclear metal-carbene complexes of the present invention comprises contacting suitable compounds comprising M with compounds of the general formula

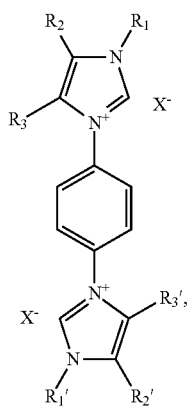

(V)

or

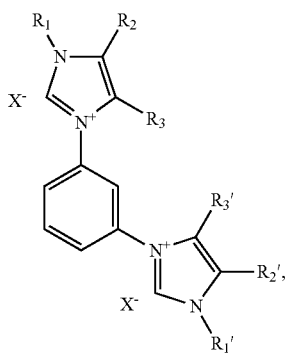

(VI)

wherein $R_1$, $R_{1'}$, $R_2$, $R_{2'}$, $R_3$ and $R_{3'}$ are each as defined above, and X is F, Cl, Br, I, $PF_6$, or $BF_4$.

Customary processes involve, for example, the deprotonation of the imidazole ligand precursors of formula (V), or (VI) and subsequent reaction, generally in situ, with suitable Pt/Pd-comprising metal compounds and optionally precursors of ligand L.

The process for preparing the inventive dinuclear metal-carbene complexes is illustrated below in more detail on basis of inventive dinuclear platinum-carbene complexes of formula I, or II, wherein L is a ligand of formula

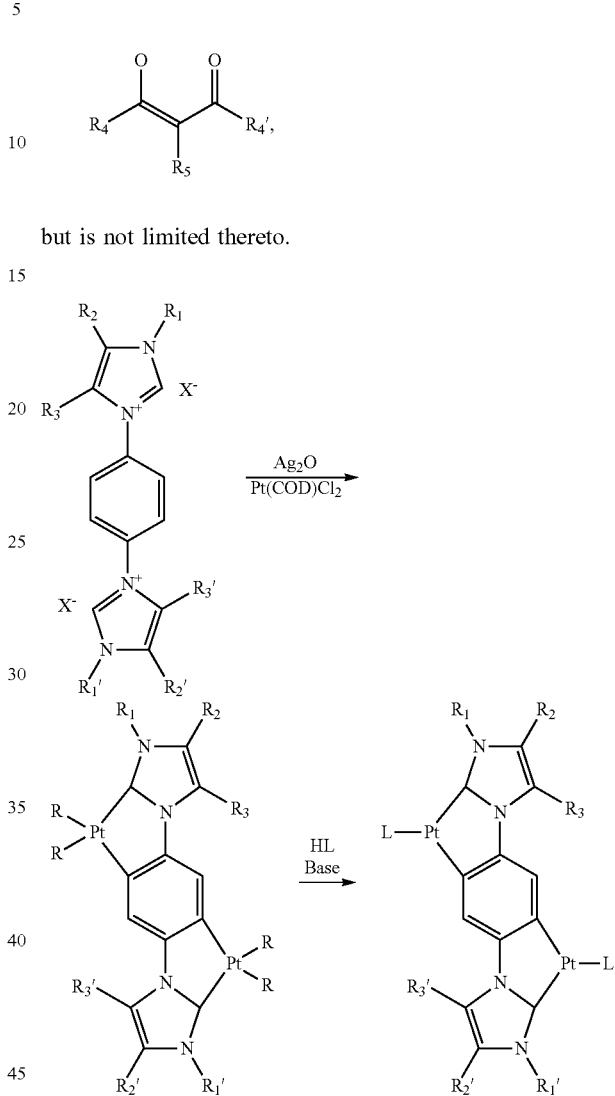

but is not limited thereto.

The process comprises the following steps:
(i) the deprotonation of the imidazole ligand precursors of formula (V), or (VI);
(ii) subsequent reaction with suitable Pt-comprising metal compounds; and
(iii) reaction of the intermediate obtained in step ii) with HL in the presence of a base.

Deprotonation in step i) can be accomplished by basic compounds known to those skilled in the art, for example basic metallates, basic metal acetates, acetylacetonates or alkoxylates, or bases such as KO$^t$Bu, NaO$^t$Bu, LiO$^t$Bu, NaH, silylamides and phosphazene bases. Preference is given to deprotonating with Ag₂O yielding a silver carbene species.

The deprotonation is preferably effected in a solvent. Suitable solvents are known per se to those skilled in the art and are preferably selected from the group consisting of aromatic and aliphatic solvents, ethers, alcohols, esters, amides, ketones, nitriles, halogenated compounds and mixtures thereof. A particularly preferred solvent is dioxane.

The reaction is effected generally at a temperature of 0 to 50° C. The reaction time depends on the desired Pt-carbene complex and is generally 1 to 80 hours, preferably 2 to 70 hours, more preferably 10 to 60 hours.

Then the deprotonated imidazole ligand precursors of formula (V), or (VI) are reacted with suitable Pt-comprising metal compounds.

In general, suitable Pt salts are all of those which are known to those skilled in the art and exhibit a sufficiently high reactivity under the inventive reaction conditions. Preference is given to corresponding Pt salts or complexes selected from the group consisting of Pt(COD)Cl$_2$ (COD=cyclooctadiene), Pt(PPh$_3$)$_2$Cl$_2$, Pt(pyridine)$_2$Cl$_2$, Pt(phenanthroline)Cl$_2$, Pt(NH$_3$)$_2$Cl$_2$, PtCl$_2$, K$_2$PtCl$_4$ and mixtures thereof, particular preference being given to using Pt(COD)Cl$_2$.

The reaction is preferably effected in a solvent. Suitable solvents are known per se to those skilled in the art and are preferably selected from the group consisting of aromatic and aliphatic solvents, ethers, alcohols, esters, amides, ketones, nitriles, halogenated compounds and mixtures thereof. A particularly preferred solvent is a mixture of dioxane and 2-butanone.

The reaction is effected generally at a temperature of 0 to 150° C. The reaction time depends on the desired Pt-carbene complex and is generally 1 to 80 hours, preferably 2 to 70 hours, more preferably 10 to 60 hours.

Afterwards all volatiles are removed and the intermediate obtained in step ii) is reacted with HL in the presence of a base, such as, for example, potassium tert-butanolate. The reaction is preferably effected in a solvent, such as, for example, dimethyl formamide.

The reaction is effected generally at a temperature of 0 to 150° C. The reaction time depends on the desired Pt-carbene complex and is generally 1 to 80 hours.

The resulting inventive dinuclear metal-carbene complex is worked up by methods known to those skilled in the art. For example, the product which precipitates out during the reaction is filtered, washed and then dried. Flash chromatography and/or recrystallization afford high-purity inventive dinuclear metal-carbene complexes.

One way to access imidazole ligands of is the reaction of an imidazole derivative with 1,3- or 1,4-dibromobenzene or 1,3- or 1,4-diiodobenzene followed by reaction with R$_1$—X as shown below for one example (e.g. Hor et al., Chem. Eur. J. (2009) 10585).

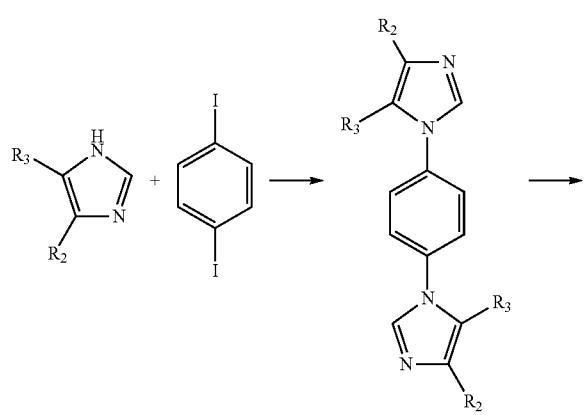

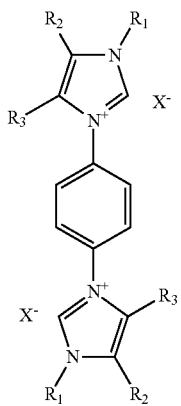

Another approach particularly suitable for R$_1$=Ar follows the method described by Fürstner et al., Chem. Comm. (2006) 2176.

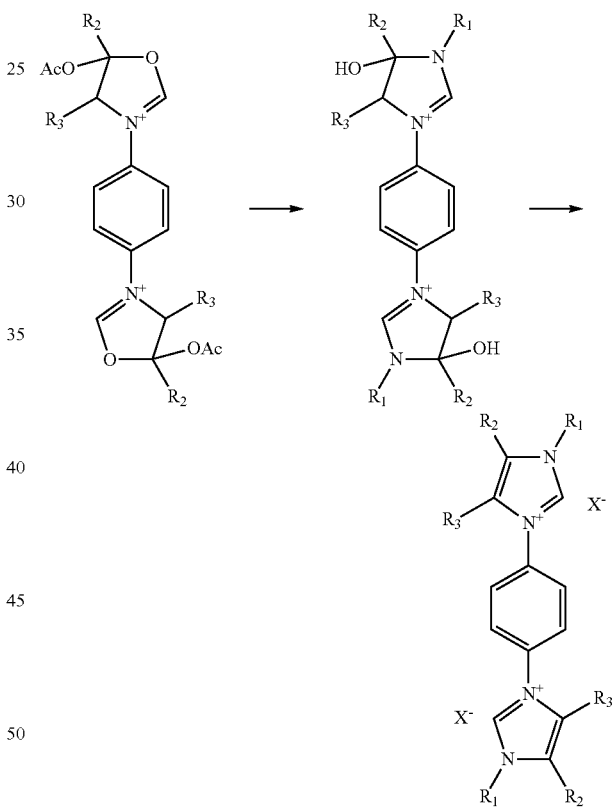

In the context of the present invention, the terms aryl radical, unit or group, heteroaryl radical, unit or group, alkyl radical, unit or group, cycloalkyl radical, unit or group, and groups with donor or acceptor action are each defined as follows—unless stated otherwise:

Aryl radicals or substituted or unsubstituted aryl radicals having 6 to 30 carbon atoms (C$_6$-C$_{30}$-aryl radicals) refer in the present invention to radicals which are derived from monocyclic, bicyclic or tricyclic aromatics which do not comprise any ring heteroatoms. When the systems are not monocyclic systems, the term "aryl" for the second ring also includes the saturated form (perhydro form) or the partly unsaturated form (for example the dihydro form or tetrahydro form), provided that the particular forms are known and stable. This means that the term "aryl" in the present invention encompasses, for example, also bicyclic or tricyclic radicals in which either both or all three radicals are aromatic, and bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl.

The aryl radicals or $C_6$-$C_{30}$-aryl radicals may be unsubstituted or substituted by one or more further radicals. Suitable further radicals are selected from the group consisting of $C_1$-$C_{20}$-alkyl, $C_6$-$C_{30}$-aryl and substituents with donor or acceptor action, suitable substituents with donor or acceptor action are specified below. The $C_6$-$C_{30}$-aryl radicals are preferably unsubstituted or substituted by one or more $C_1$-$C_{20}$-alkyl groups, $C_1$-$C_{20}$-alkoxy groups, CN, $CF_3$, F or amino groups ($NR^{62}R^{63}$ where suitable $R^{62}$ and $R^{63}$ radicals are specified below).

Heteroaryl radicals or substituted or unsubstituted heteroaryl radicals having a total of 5 to 18 carbon atoms and/or heteroatoms are understood to mean monocyclic, bicyclic or tricyclic heteroaromatics, some of which can be derived from the aforementioned aryl, in which at least one carbon atom in the aryl base structure has been replaced by a heteroatom. Preferred heteroatoms are N, O and S. The heteroaryl radicals more preferably have 5 to 13 ring atoms. The base structure of the heteroaryl radicals is especially preferably selected from systems such as pyridine and five-membered heteroaromatics such as thiophene, pyrrole, imidazole, thiazole, oxazole or furan. These base structures may optionally be fused to one or two six-membered aromatic radicals. Suitable fused heteroaromatics are carbazolyl, benzimidazolyl, benzofuryl, benzothiazolyl, benzoxazolyl, dibenzofuryl or dibenzothiophenyl.

The base structure may be substituted at one, more than one or all substitutable positions, suitable substituents being the same as those already specified under the definition of $C_6$-$C_{30}$-aryl. However, the heteroaryl radicals are preferably unsubstituted. Suitable heteroaryl radicals are, for example, pyridin-2-yl, pyridin-3-yl, pyridin-4-yl, thiophen-2-yl, thiophen-3-yl, pyrrol-2-yl, pyrrol-3-yl, furan-2-yl, furan-3-yl, thiazol-2-yl, oxazol-2-yl and imidazol-2-yl, and the corresponding benzofused radicals, especially carbazolyl, benzimidazolyl, benzofuryl, benzothiazolyl, benzoxazolyl, dibenzofuryl or dibenzothiophenyl.

An alkyl radical in the context of the present application is a linear or branched alkyl radical optionally bearing at least one functional group, optionally interrupted by at least one heteroatom and having 1 to 20 carbon atoms. Preference is given to $C_1$- to $C_{10}$-alkyl radicals, particular preference to $C_1$- to $C_6$-alkyl radicals. In addition, the alkyl radicals may be substituted by one or more functional groups, preferably selected from the group consisting of $C_1$-$C_{20}$-alkyl, $C_1$-$C_{20}$-alkoxy, halogen, preferably F, $C_1$-$C_{20}$-haloalkyl, e.g. $CF_3$, and $C_6$-$C_{30}$-aryl which may in turn be substituted or unsubstituted. Suitable aryl substituents and suitable alkoxy and halogen substituents are specified below. Examples of suitable alkyl groups are methyl, ethyl, propyl, butyl, pentyl, hexyl, heptyl and octyl, and also $C_1$-$C_{20}$-alkyl, $C_1$-$C_{20}$-haloalkyl, $C_6$-$C_{30}$-aryl-, $C_1$-$C_{20}$-alkoxy- and/or halogen-substituted, especially F-substituted, derivatives of the alkyl groups mentioned, for example $CF_3$. This comprises both the n-isomers of the radicals mentioned and branched isomers such as isopropyl, isobutyl, isopentyl, sec-butyl, tert-butyl, neopentyl, 3,3-dimethylbutyl, 3-ethylhexyl, etc. Preferred alkyl groups are methyl, ethyl, isopropyl, tert-butyl and $CF_3$.

A cycloalkyl radical or a substituted or unsubstituted cycloalkyl radical having 3 to 20 carbon atoms is understood in the context of the present application to mean a substituted or unsubstituted $C_3$-$C_{20}$-cycloalkyl radical. Preferred are cycloalkyl radicals having 5 to 20, more preferably 5 to 10 and most preferably 5 to 8 carbon atoms in the base structure (ring) to understand. Suitable substituents are the substituents mentioned for the alkyl groups. Examples of suitable cycloalkyl groups, which may be unsubstituted or substituted by the radicals mentioned above for the alkyl groups, are cyclopentyl, cyclohexyl, cycloheptyl, cyclooctyl, cyclononyl and cyclodecyl. They may also be polycyclic ring systems such as decalinyl, norbornyl, bornanyl or adamantyl.

Suitable alkoxy radicals derive correspondingly from the aforementioned alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. In this context, $C_3H_7$, $C_4H_9$ and $C_8H_{17}$ comprise both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

In the context of the present application, groups with donor or acceptor action are understood to mean the following groups:

$C_1$-$C_{20}$-alkoxy, $C_6$-$C_{30}$-aryloxy, $C_6$-$C_{30}$-arylthio, $SiR^{64}R^{65}R^{66}$, halogen radicals, halogenated $C_1$-$C_{20}$-alkyl radicals, carbonyl (—CO($R^{64}$)), carbonylthio (—C=O($SR^{64}$)), carbonyloxy (—C=O($OR^{64}$)), oxycarbonyl (—OC=O($R^{64}$)), thiocarbonyl (—SC=O($R^{64}$)), amino (—$NR^{64}R^{65}$), OH, pseudohalogen radicals, amido (—C=O($NR^{64}R^{65}$)), —$NR^{64}$C=O($R^{65}$), phosphonate (—P(O)($OR^{64}$)$_2$, phosphate (—OP(O)($OR^{64}$)$_2$), phosphine (—$PR^{64}R^{65}$), phosphine oxide (—P(O)$R^{64}_2$), sulfate (—OS(O)$_2OR^{64}$), sulfoxide (—S(O)$R^{64}$), sulfonate (—S(O)$_2OR^{64}$), sulfonyl (—S(O)$_2R^{64}$), sulfonamide (—S(O)$_2NR^{64}R^{65}$), $NO_2$, boronic esters (—OB($OR^{64}$)$_2$), imino (—C=$NR^{64}R^{65}$)), borane radicals, stannate radicals, hydrazine radicals, hydrazone radicals, oxime radicals, nitroso groups, diazo groups, vinyl groups, sulfoximines, alanes, germanes, boroxines and borazines.

Preferred substituents with donor or acceptor action are selected from the group consisting of: $C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{64}R^{65}R^{66}$, where $R^{64}$, $R^{65}$ and $R^{66}$ are preferably each independently substituted or unsubstituted alkyl or substituted or unsubstituted phenyl, suitable substituents having been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —C(O)OC$_1$-C$_4$-alkyl, preferably —C(O)OMe, P(O)R$^2$, preferably P(O)Ph$_2$, and SO$_2$R$^2$, preferably SO$_2$Ph.

Very particularly preferred substituents with donor or acceptor action are selected from the group consisting of methoxy, phenyloxy, halogenated C$_1$-C$_4$-alkyl, preferably CF$_3$, CH$_2$F, CHF$_2$, C$_2$F$_5$, halogen, preferably F, CN, SiR$^{64}$R$^{65}$R$^{66}$, where suitable R$^{64}$, R$^{65}$ and R$^{66}$ radicals have been specified above, diphenylamino, —C(O)OC$_1$-C$_4$-alkyl, preferably —C(O)OMe, P(O)Ph$_2$ and SO$_2$Ph.

The aforementioned groups with donor or acceptor action are not intended to rule out the possibility that further radicals and groups among those specified above may also have donor or acceptor action. For example, the aforementioned heteroaryl radicals are likewise groups with donor or acceptor action, and the C$_1$-C$_{20}$-alkyl radicals are groups with donor action.

The inventive dinuclear metal-carbene complexes can be used in electronic components, for example organic electronic components selected from switching elements such as organic light-emitting diodes (OLEDs), organic photovoltaic cells (OPVs), organic field-effect transistors (OFETs) and light-emitting electrochemical cells (LEECs), preference being given to using the metal-carbene complexes of the formula (I) in OLEDs.

In a preferred embodiment, the organic electronic component is an OLED comprising a light-emitting layer comprising at least one inventive dinuclear metal-carbene complex.

The aforementioned inventive dinuclear metal-carbene complexes and mixtures thereof are outstandingly suitable as emitter molecules in organic light-emitting diodes (OLEDs).

Variations in the ligands make it possible to provide corresponding complexes which exhibit electroluminescence in a wide range of the electromagnetic spectrum. The inventive dinuclear metal-carbene complexes are therefore outstandingly suitable as emitter substances and it is thus possible, with the aid of the inventive complexes as emitter substances, to provide industrially usable OLEDs.

In addition, the inventive dinuclear metal-carbene complexes can be used as matrix material, charge transport material, especially hole transport material, and/or charge blocker.

The inventive dinuclear metal-carbene complexes are preferably used as an emitter and/or charge transport material and/or matrix material, more preferably as an emitter.

Particular properties of the inventive dinuclear metal-carbene complexes are particularly good efficiencies, good CIE color loci and long lifetimes when used in OLEDs.

The present application therefore further provides an OLED comprising at least one inventive dinuclear metal-carbene complex. The inventive dinuclear metal-carbene complex is used in the OLED preferably as an emitter, matrix material, charge transport material, especially hole transport material, and/or charge blocker, more preferably as an emitter and/or hole transport material, most preferably as an emitter.

The present application also provides for the use of the inventive dinuclear metal-carbene complexes in OLEDs, preferably as an emitter, matrix material, charge transport material, especially hole transport material, and/or charge blocker, more preferably as an emitter and/or hole transport material, most preferably as an emitter.

Organic light-emitting diodes are in principle formed from a plurality of layers, e.g.:
anode (1)
hole-transporting layer (2)
light-emitting layer (3)
electron-transporting layer (4)
cathode (5)

It is, however, also possible that the OLED does not have all of the layers mentioned; for example, an OLED comprising layers (1) (anode), (3) (light-emitting layer) and (5) (cathode) is likewise suitable, in which case the functions of layers (2) (hole-transporting layer) and (4) (electron-transporting layer) are assumed by the adjoining layers. OLEDs having layers (1), (2), (3) and (5) or layers (1), (3), (4) and (5) are likewise suitable.

The inventive dinuclear metal-carbene complexes are preferably used as emitter molecules and/or matrix materials in the light-emitting layer (3). The inventive dinuclear metal-carbene complexes may—in addition to use as emitter molecules and/or matrix materials in the light-emitting layer (3) or instead of use in the light-emitting layer—also be used as a charge transport material in the hole-transporting layer (2) or in the electron-transporting layer (4) and/or as a charge blocker, preference being given to use as a charge transport material in the hole-transporting layer (2) (hole transport material).

The present application therefore further provides a light-emitting layer comprising at least one of the inventive dinuclear metal-carbene complexes, preferably as emitter material and/or matrix material, more preferably as emitter material. Preferred inventive dinuclear metal-carbene complexes have already been specified above.

In a further embodiment, the present invention relates to a light-emitting layer consisting of at least one inventive dinuclear metal-carbene complex.

The inventive dinuclear metal-carbene complexes used in accordance with the invention may be present in the light-emitting layer in substance, i.e. without further additions. However, it is also possible that, in addition to the dinuclear metal-carbene complexes used in accordance with the invention, further compounds are present in the light-emitting layer. In addition, a diluent material (matrix material) may be used. This diluent material may be a polymer, for example poly(N-vinylcarbazole) or polysilane. The diluent material may, however, likewise be a small molecule, for example 4,4'-N,N'-dicarbazolebiphenyl (CDP) or tertiary aromatic amines. When a diluent material is used, the proportion of the inventive dinuclear metal-carbene complexes in the light-emitting layer is generally less than 40% by weight, preferably 3 to 30% by weight. The inventive dinuclear metal-carbene complexes are preferably used in a matrix. The light-emitting layer thus preferably comprises at least one inventive dinuclear metal-carbene complex and at least one matrix material.

Suitable matrix materials are—in addition to the aforementioned dilution materials—in principle the materials specified hereinafter as hole and electron transport materials, and also carbon complexes, for example, the inventive dinuclear metal-carbene complexes, or the carbene complexes mentioned in WO 2005/019373. Particularly suitable are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the matrix materials specified in the following applications: WO2008/034758, WO2009/003919.

Further suitable matrix materials, which may be small molecules or (co)polymers of the small molecules mentioned, are specified in the following publications:

WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co)polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co)polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co)polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446 and WO06128800.

In a particularly preferred embodiment, one or more compounds of the general formula (X) specified hereinafter are used as matrix material. Preferred embodiments of the compounds of the general formula (X) are likewise specified hereinafter.

The individual layers among the aforementioned layers of the OLED may in turn be formed from two or more layers. For example, the hole-transporting layer may be formed from one layer, into which holes are injected from the electrode, and a layer which transports the holes away from the hole-injecting layer into the light-emitting layer. The electron-transporting layer may likewise consist of a plurality of layers, for example of a layer in which electrons are injected through the electrode and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the inventive dinuclear metal-carbene complexes used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be formed from any material which is typically used in such layers and is known to those skilled in the art.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices* in *Organic Light-Emitting Materials and Devices*, eds: Z. Li, H. Meng, Taylor & Francis, 2007, Chapter 3, pages 295 to 411.

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole transport material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis [(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenyl-hydrazone (DEH), triphenylamine (TPA), bis[4-(N,N-diethylamino)-2-methylphenyl](4-methylphenyl)methane (MPMP), 1-phenyl-3-[p-

(diethylamino)styryl]-5-[p-(diethylamino)phenyl]pyrazoline (PPR or DEASP), 1,2-trans-bis(9H-carbazol-9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino-9,9-spirobifluorene (spiro-TTB), N,N'-bis(naphthalen-1-yl)-N,N'-bis(phenyl)-9,9-spirobifluorene (spiro-NPB) and 9,9-bis(4-(N,N-bis-biphenyl-4-yl-amino)phenyl-9H-fluorene, benzidine compounds such as N,N'-bis(naphthalen-1-yl)-N,N'-bis(phenyl)-benzidine and porphyrin compounds such as copper phthalocyanines. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

In addition—in one embodiment—it is possible to use the inventive dinuclear metal carbene complexes as hole conductor materials, in which case the band gap of the at least one hole conductor material is generally greater than the band gap of the emitter material used. In the context of the present application, band gap is understood to mean the triplet energy. Suitable carbene complexes are, for example, the inventive carbene complexes of the general formula (I), carbene complexes as described in WO2005/019373, WO2006/056418, WO2005/113704, WO2007/115970, WO2007/115981 and WO2008/000727. One example of a suitable carbene complex is Ir(DPBIC)$_3$ with the formula:

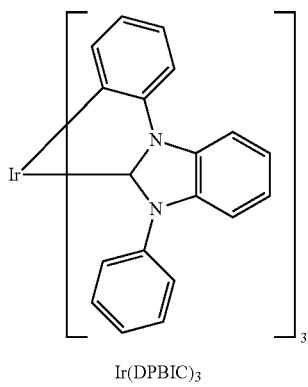

Ir(DPBIC)$_3$

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example MoO$_2$, MoO$_3$, WO$_x$, ReO$_3$ and/or V$_2$O$_5$, preferably MoO$_3$ and/or ReO$_3$, more preferably ReO$_3$ or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane (F$_4$-TCNQ), 2,5-bis(2-hydroxyethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-etracyanoquinodimethane, dicyanomethylene-1,3,4,5,7,8-hexafluoro-6H-naphthalen-2-ylidene)malononitrile (F$_6$-TNAP), Mo(tfd)$_3$ (from Kahn et al., J. Am. Chem. Soc. 2009, 131 (35), 12530-12531), compounds as described in EP1988587 and in EP2180029 and quinone compounds as mentioned in EP2401254.

Suitable electron-transporting materials for layer (4) of the inventive OLEDs comprise metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer (4) may serve both to ease the electron transport and as a buffer layer or as a barrier layer in order to prevent quenching of the exciton at the interfaces of the layers of the OLED. Layer (4) preferably improves the mobility of the electrons and reduces quenching of the exciton.

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIaa) below. More preferably, in mixed electron-transporting layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII). Reference is made to WO2011/157779.

The electron-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, Cs$_2$CO$_3$, with alkali metal complexes, for example 8-hydroxyquinolatolithium (Liq), and with Y, Ce, Sm, Gd, Tb, Er, Tm, Yb, Li$_3$N, Rb$_2$CO$_3$, dipotassium phthalate, W(hpp)$_4$ from EP 1786050, or with compounds as described in EP1837926B1.

The present invention therefore also relates to an inventive OLED which comprises an electron-transporting layer comprising at least two different materials, of which at least one material is electron-conducting.

In a preferred embodiment, the electron-transporting layer comprises at least one compound of the general formula (VII)

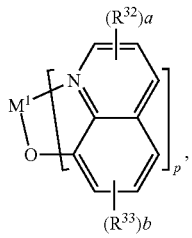

in which
$R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or
two $R^{32}$ and/or $R^{33}$ substituents together form a fused benzene ring which is optionally substituted by one or more $C_1$-$C_8$-alkyl groups;
a and b are each independently 0, or 1, 2 or 3,
$M^1$ is an alkaline metal atom or alkaline earth metal atom, p is 1 when $M^1$ is an alkaline metal atom, p is 2 when $M^1$ is an alkaline earth metal atom.

A very particularly preferred compound of the formula (VII) is

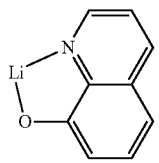

(Liq), which may be present as a single species, or in other forms such as Li$_g$Q$_g$ in which g is an integer, for example Li$_6$Q$_6$. Q is an 8-hydroxyquinolate ligand or an 8-hydroxyquinolate derivative.

In a further preferred embodiment, the electron-transporting layer comprises at least one compound of the formula (VIII),

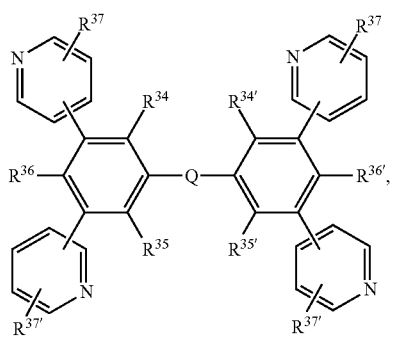

(VIII)

in which
$R^{34}$, $R^{35}$, $R^{36}$, $R^{37}$, $R^{34'}$, $R^{35'}$, $R^{36'}$ and $R^{37'}$ are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;
D is —CO—; —COO—; —S—; —SO—; —SO$_2$—; —O—; —NR$^{40}$—; —SiR$^{45}$R$^{46}$—; —POR$^{47}$—; —CR$^{38}$=CR$^{39}$—; or —C≡C—;
E is —OR$^{44}$; —SR$^{44}$; —NR$^{40}$R$^{41}$; —COR$^{43}$; —COOR$^{42}$; —CONR$^{40}$R$^{41}$; —CN; or F;
G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D,
in which
$R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;
$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or
$R^{40}$ and $R^{41}$ together form a 6-membered ring;
$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—,
$R^{44}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—,
$R^{45}$ and $R^{46}$ are each independently $C_1$-$C_{18}$-alkyl, $C_6$-$C_{18}$-aryl or $C_6$-$C_{18}$-aryl which is substituted by $C_1$-$C_{18}$-alkyl,
$R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

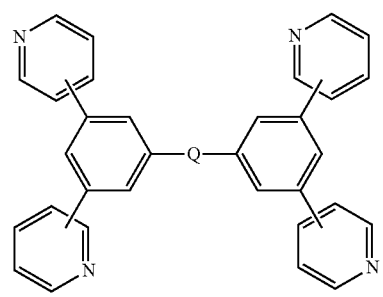

(VIIIa)

in which Q is:

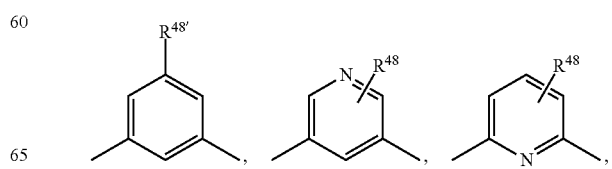

or

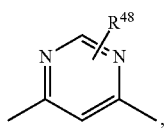

R⁴⁸ is H or $C_1$-$C_{18}$-alkyl and
R⁴⁸' is H, $C_1$-$C_{18}$-alkyl or

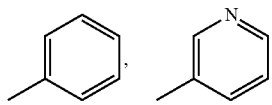

or

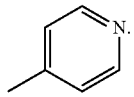

Particular preference is given to a compound of the formula (VIIIaa)

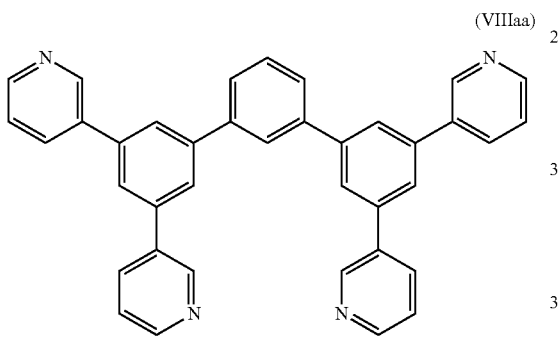
(VIIIaa)

In a further, very particularly preferred embodiment, the electron-transporting layer comprises a compound of the formula

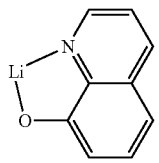

(Liq) and a compound of the formula

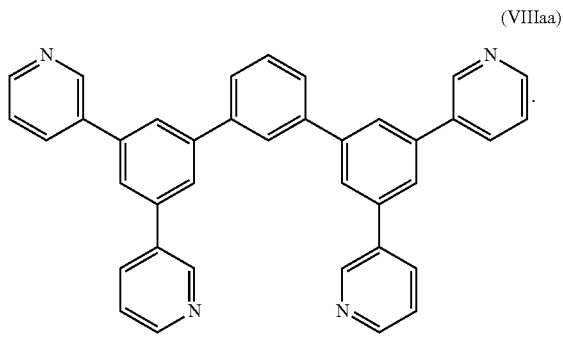 [SMILES: c1cncc(-c2cc(-c3cccnc3)cc(-c3cccc(-c4cc(-c5cccnc5)cc(-c5cccnc5)c4)c3)c2)c1]
(VIIIaa)

In a preferred embodiment, the electron-transporting layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

It is likewise possible to use mixtures of alkali metal hydroxyquinolate complexes, preferably Liq, and dibenzofuran compounds in the electron-transporting layer. Reference is made to WO2011/157790. Dibenzofuran compounds A-1 to A-36 and B-1 to B-22 described in WO2011/157790 are preferred, wherein dibenzofuran compound

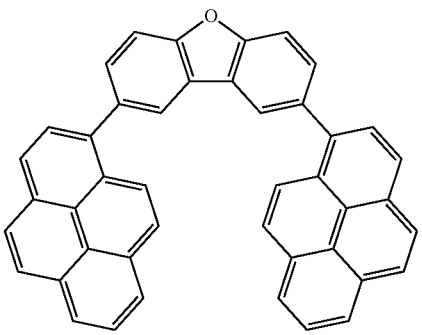
(A-10)

is most preferred.

In a preferred embodiment, the electron-transporting layer comprises Liq in an amount of 99 to 1% by weight, preferably 75 to 25% by weight, more preferably about 50% by weight, where the amount of Liq and the amount of the dibenzofuran compound(s), especially

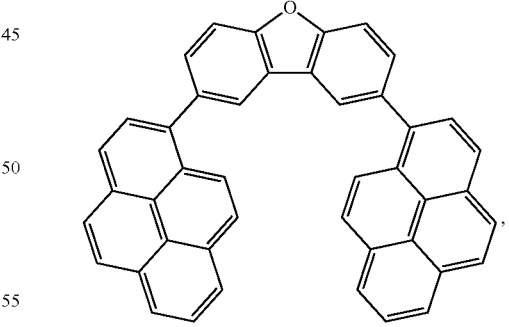

adds up to a total of 100% by weight.

The preparation of the compounds of the formula (VII) is described, for example, in Christoph Schmitz et al. Chem. Mater. 12 (2000) 3012-3019 and WO00/32717, or the compounds can be prepared analogously to the processes disclosed in the aforementioned documents.

In a preferred embodiment, the invention relates to an inventive OLED wherein the electron-transporting layer comprises at least one phenanthroline derivative and/or pyridine derivative.

In a further preferred embodiment, the invention relates to an inventive OLED wherein the electron-transporting layer comprises at least one phenanthroline derivative and/or pyridine derivative and at least one alkali metal hydroxyquinolate complex.

In a further preferred embodiment, the invention relates to an inventive OLED wherein the electron-transporting layer comprises at least one phenanthroline derivative and/or pyridine derivative and 8-hydroxyquinolatolithium.

Some of the materials mentioned above as hole transport materials and electron-transporting materials can fulfill several functions. For example, some of the electron-transporting materials are simultaneously hole-blocking materials if they have a low-lying HOMO.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li and Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds such as 8-hydroxyquinolatolithium (Liq), CsF, NaF, KF, $Cs_2CO_3$ or LiF may be applied between the organic layer and the cathode as an electron injection layer in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:
- a hole injection layer between the anode (1) and the hole-transporting layer (2) (thickness: 50 to 1000 Å, preferably 200 to 800 Å);
- a blocking layer for electrons between the hole-transporting layer (2) and the light-emitting layer (3) (thickness: 10 to 500 Å, preferably 50 to 100 Å);
- a blocking layer for holes between the light-emitting layer (3) and the electron-transporting layer (4) (thickness: 10 to 500 Å, preferably 50 to 100 Å);
- an electron injection layer between the electron-transporting layer (4) and the cathode (5) (thickness: 10 to 500 Å, preferably 20 to 100 Å).

As already mentioned above, however, it is also possible that the OLED does not have all of the layers (1) to (5) mentioned; for example, an OLED comprising layers (1) (anode), (3) (light-emitting layer) and (5) (cathode) is likewise suitable, in which case the functions of layers (2) (hole-transporting layer) and (4) (electron-transporting layer) are assumed by the adjoining layers. OLEDs having layers (1), (2), (3) and (5) or layers (1), (3), (4) and (5) are likewise suitable.

Those skilled in the art know how suitable materials have to be selected (for example on the basis of electrochemical investigations). Suitable materials for the individual layers are known to those skilled in the art and disclosed, for example, in WO00/70655.

In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

It is possible that the layers of the OLED are all produced by the same coating method. Furthermore, it is likewise possible to conduct two or more different coating methods to produce the layers of the OLED.

In general, the different layers have the following thicknesses: anode (2) 500 to 5000 Å, preferably 1000 to 2000 Å (ångström); hole-transporting layer (3) 50 to 1000 Å, preferably 200 to 800 Å; light-emitting layer (4) 10 to 1000 Å, preferably 100 to 800 Å; electron-transporting layer (5) 50 to 1000 Å, preferably 200 to 800 Å; cathode (6) 200 to 10 000 Å, preferably 300 to 5000 Å. In addition, it is likewise possible to combine several layers by mixing. For example, the hole-transporting material can be mixed with the materials of the light-emitting layer and then applied together. The position of the recombination zone of holes and electrons in the inventive OLED and thus the emission spectrum of the OLED may be influenced by the relative thickness and concentration ratios of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

In a preferred embodiment, the present invention relates to an OLED comprising at least one inventive metal-carbene complex, and at least one compound of the general formula

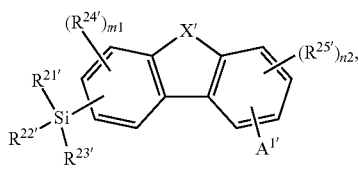

wherein X' is NR, S, O or PR$^{26'}$;
R$^{26'}$ is aryl, heteroaryl, alkyl, cycloalkyl, or heterocycloalkyl;
A$^{1'}$ is —NR$^{6'}$ R$^{7'}$, —P(O)R$^{8'}$ R$^{9'}$, PR$_{10'}$ R$^{11'}$, —S(O)$_2$R$_{12'}$, —S(O)R$_{13'}$, —SR$_{14'}$, or —OR$_{15'}$;
R$^{21'}$, R$^{22'}$ and R$^{23'}$ are independently of each other aryl, heteroaryl, alkyl, cycloalkyl, or heterocycloalkyl, wherein at least on of the groups R$^{21'}$, R$^{22'}$, or R$^{23'}$ is aryl, or heteroaryl;
R$^{24'}$ and R$^{25'}$ are independently of each other alkyl, cycloalkyl, heterocycloalkyl, aryl, heteroaryl, a group A$^{1'}$, or a group having donor, or acceptor characteristics;
n2 and m1 are independently of each other 0, 1, 2, or 3;
R$^{6'}$ and R$^{7'}$ form together with the nitrogen atom a cyclic residue having 3 to 10 ring atoms, which can be unsubstituted, or which can be substituted with one, or more substituents selected from alkyl, cycloalkyl, heterocycloalkyl, aryl, heteroaryl and a group having donor, or acceptor characteristics; and/or which can be annulated with one, or more further cyclic residues having 3 to 10 ring atoms, wherein the annulated residues can be unsubstituted, or can be substituted with one, or more substituents selected from alkyl, cycloalkyl, heterocycloalkyl, aryl, heteroaryl and a group having donor, or acceptor characteristics; and
R$^{8'}$, R$^{9'}$, R$_{10'}$, R$_{11'}$, R$_{12'}$, R$_{13'}$, R$_{14'}$ and R$_{15'}$ are independently of each other aryl, heteroaryl, alkyl, cycloalkyl, or heterocycloalkyl. Compounds of formula X, such as, for example,

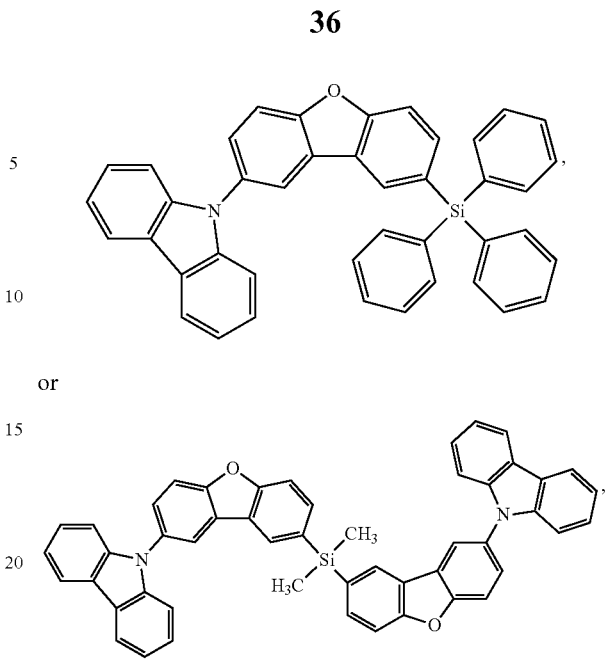

are described in WO2010079051 (in particular pages on 19 to 26 and in tables on pages 27 to 34, pages 35 to 37 and pages 42 to 43).

Additional matrix materials on basis of dibenzofurane are, for example, described in US2009066226, EP1885818B1, EP1970976, EP1998388 and EP2034538. Examples of particularly preferred matrix materials are shown below:

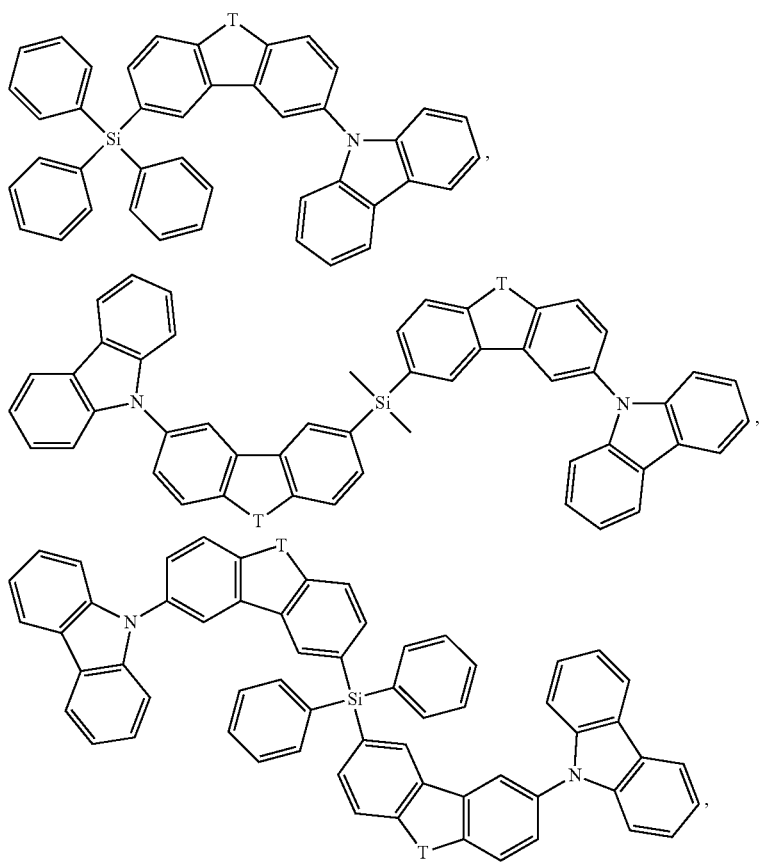

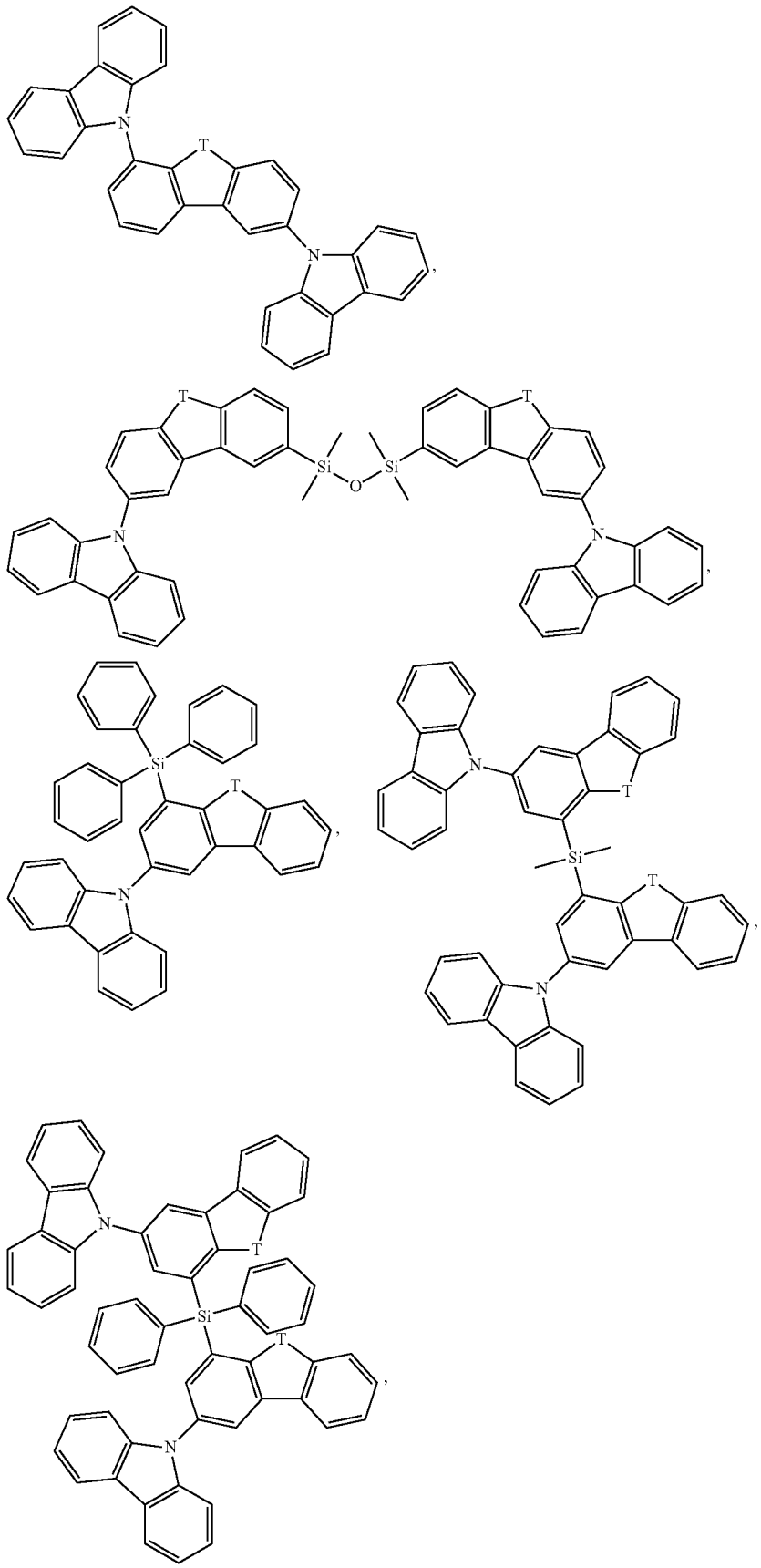

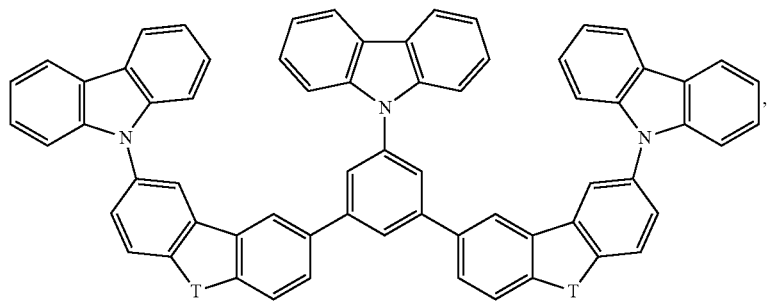
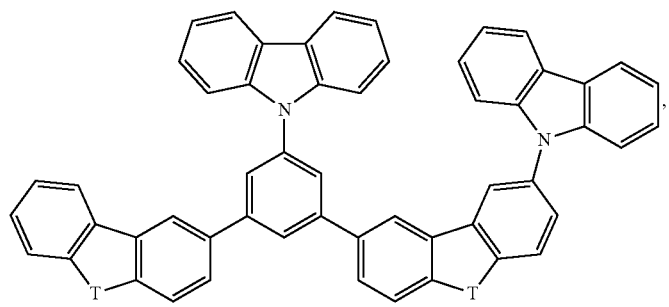
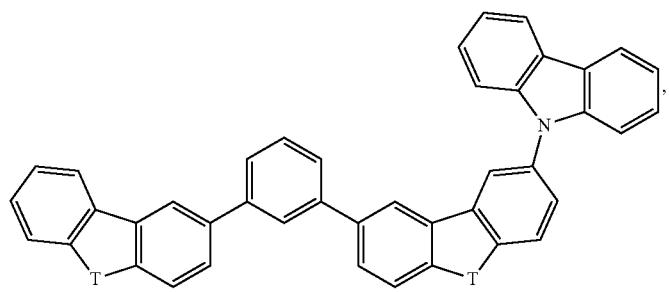
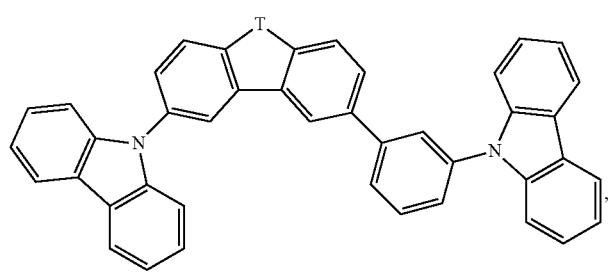
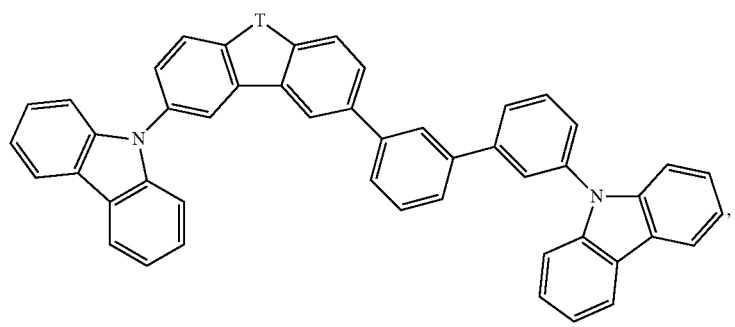

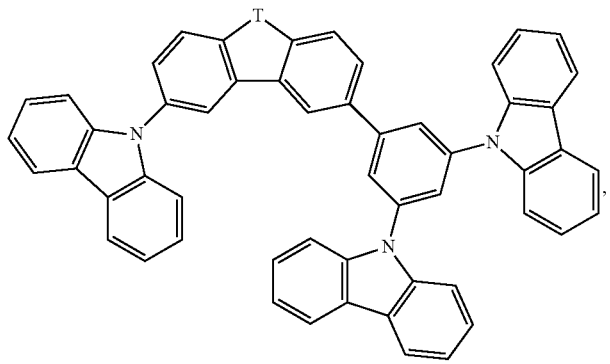
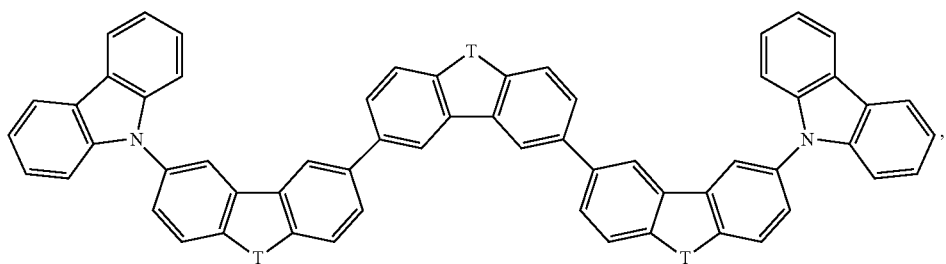
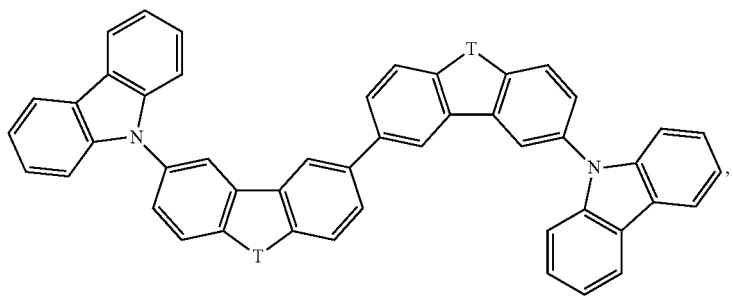
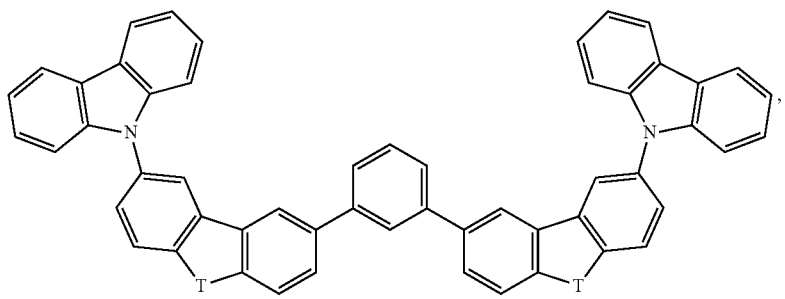
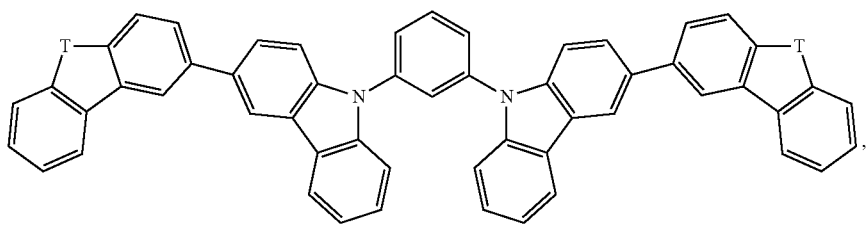

-continued
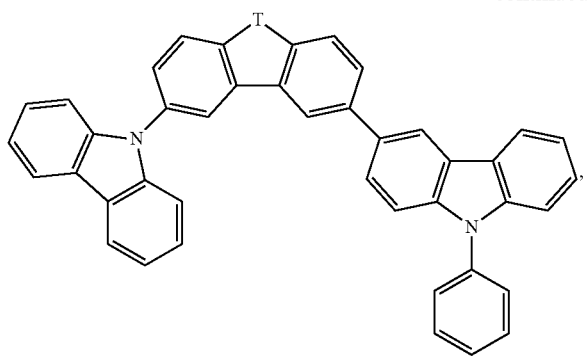
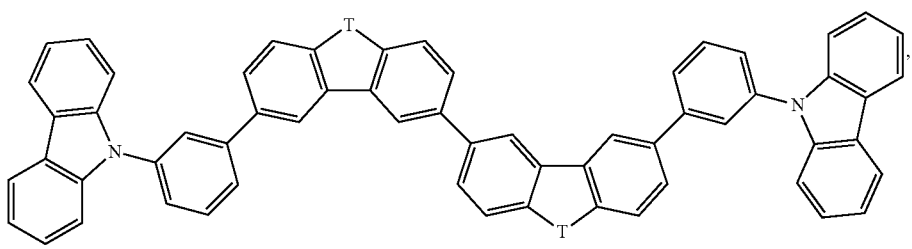
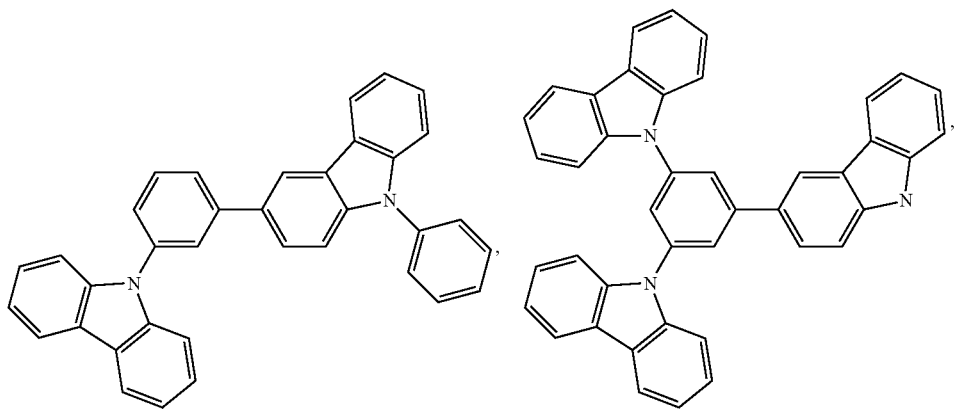
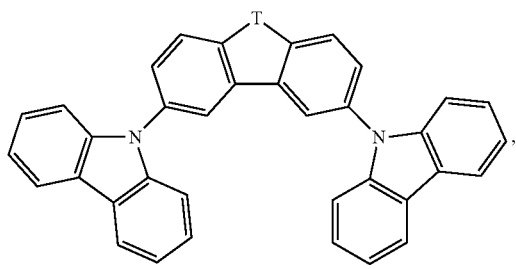
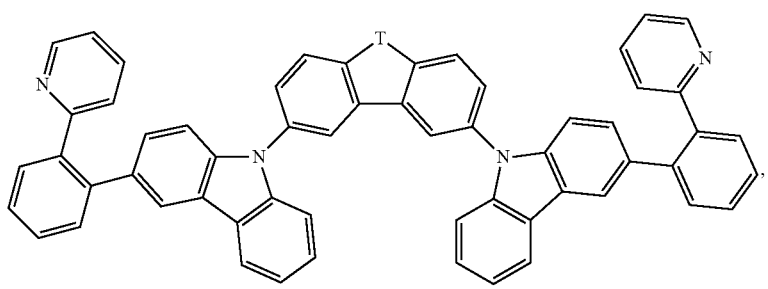

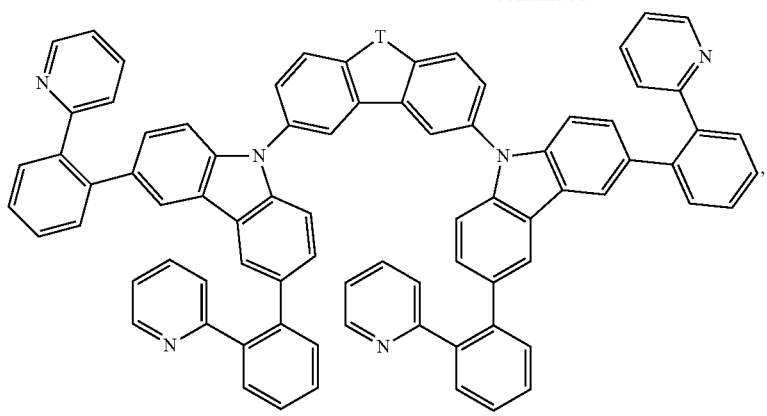
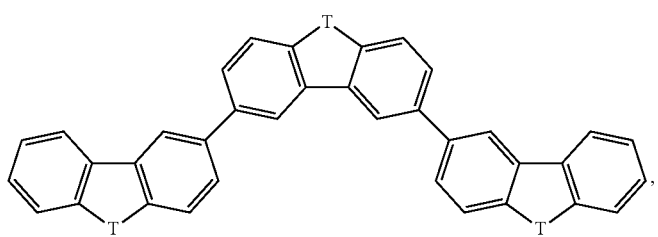
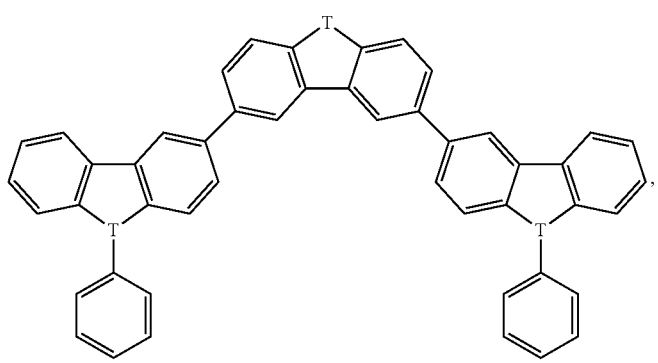
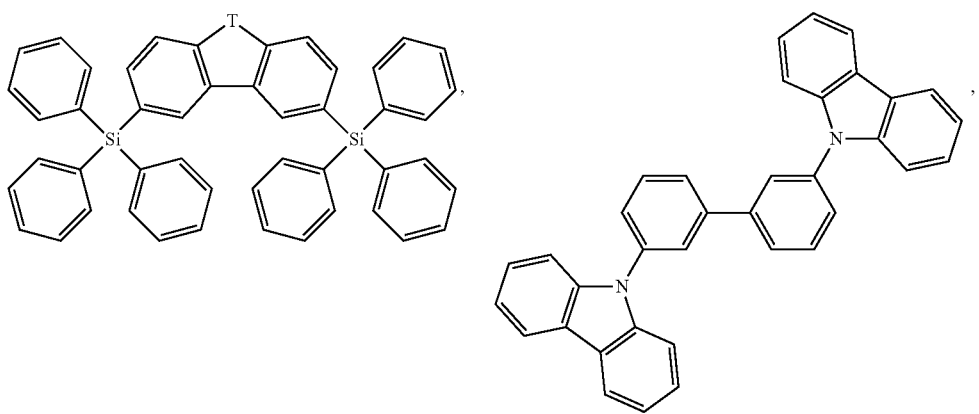

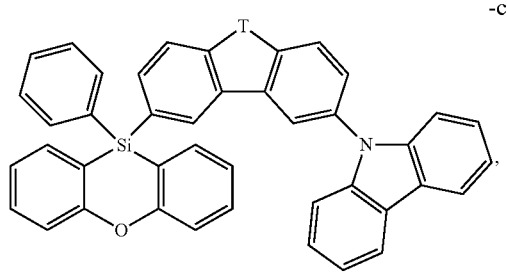
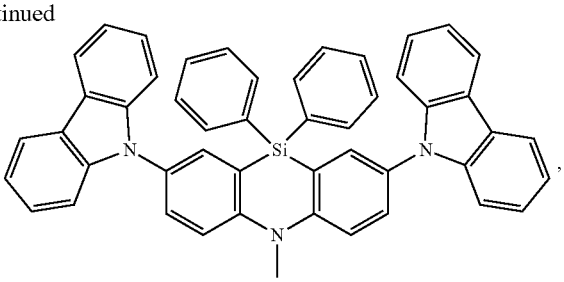

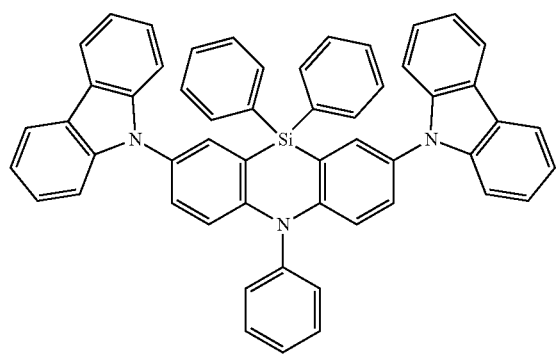

and

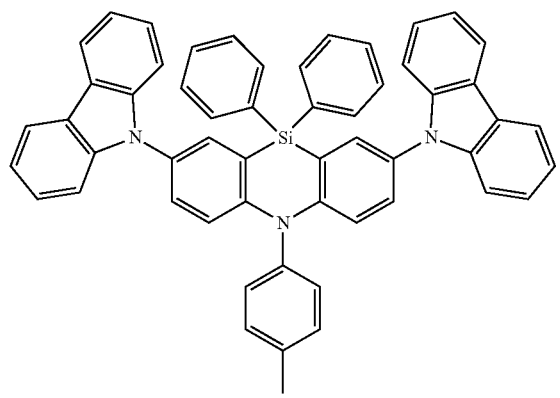

In the above-mentioned compounds T is O, or S, preferably O. If T occurs more than one time in a molecule, all groups T have the same meaning.

In a preferred embodiment, the light-emitting layer is formed from 2 to 40% by weight, preferably 5 to 35% by weight, of at least one of the inventive dinuclear metal carbon complexes and 60 to 98% by weight, preferably 65 to 95% by weight, of at least one of the aforementioned matrix materials, where the sum total of the emitter material and of the matrix material adds up to 100% by weight.

In particularly preferred embodiment, the light-emitting layer comprises a matrix material, such as, for example,

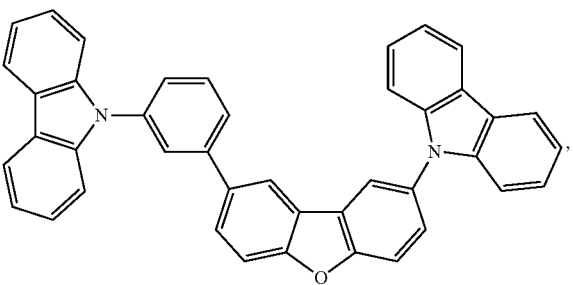

(Ma1)

and two carbene complexes, preferably of formula

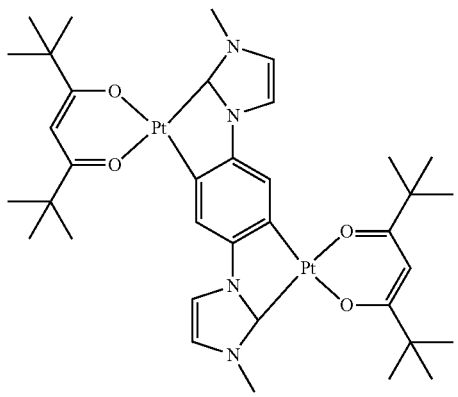
(EM2)

and

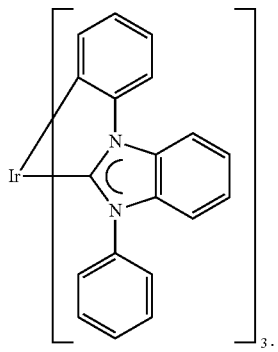

In said embodiment, the light-emitting layer is formed from 2 to 40% by weight, preferably 5 to 35% by weight, of EMI and 60 to 98% by weight, preferably 65 to 95% by weight, of Ma1 and

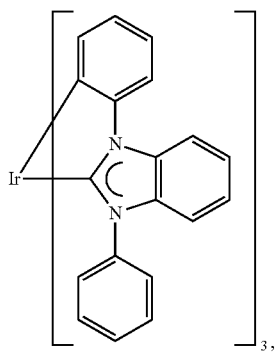

where the sum total of the carbon complexes and Ma1 adds up to 100% by weight.

Suitable metal complexes for use as matrix material and/or hole/exciton blocker material and/or electron/exciton blocker material and/or hole injection material and/or electron injection material and/or hole transport material and/or electron transport material, preferably as matrix material and/or hole/exciton blocker material, in OLEDs are thus, for example, also carbene complexes as described in WO2005/019373, WO2006/056418, WO 2005/113704, WO 2007/115970, WO 2007/115981 and WO 2008/000727. Explicit reference is made here to the disclosure of the WO applications cited, and these disclosures shall be considered to be incorporated into the content of the present application.

In addition to the compounds of the formula (X), according to the present invention, it is also possible to use crosslinked or polymeric materials comprising repeat units based on the general formula (X) in crosslinked or polymerized form together with at least one inventive dinuclear metal-carbene complex. Like the compounds of the general formula (X), the latter are preferably used as matrix materials.

The crosslinked or polymeric materials have outstanding solubility in organic solvents, excellent film-forming properties and relatively high glass transition temperatures. In addition, high charge carrier mobilities, high stabilities of color emission and long operating times of the corresponding components can be observed when crosslinked or polymeric materials according to the present invention are used in organic light-emitting diodes (OLEDs).

The crosslinked or polymerized materials are particularly suitable as coatings or in thin films since they are thermally and mechanically stable and relatively defect-free.

The crosslinked or polymerized materials comprising repeating units based on the general formula (X) can be prepared by a process comprising steps (a) and (b):
(a) preparation of a crosslinkable or polymerizable compound of the general formula (x) where at least one of the m1 $R^{24}$ radicals or at least one of the n2 $R^{25}$ radicals is a crosslinkable or polymerizable group attached via a spacer, and
(b) crosslinking or polymerization of the compound of the general formula (X) obtained from step (a).

The crosslinked or polymerized materials may be homopolymers, which means that exclusively units of the general formula (X) are present in crosslinked or polymerized form. They may also be copolymers, which means that further monomers are present in addition to the units of the general formula (X), for example monomers with hole-conducting and/or electron-conducting properties, in crosslinked or polymerized form.

In a further preferred embodiment of the inventive OLED, it comprises an emission layer comprising at least one inventive dinuclear metal-carbene complex, at least one matrix material of the formula (X), and optionally at least one further hole-transporting matrix material.

The inventive OLEDs can be used in all devices in which electroluminescence is useful. Suitable devices are preferably selected from stationary and mobile visual display units and illumination means. The present invention therefore also relates to a device selected from the group consisting of stationary visual display units and mobile visual display units and illumination means, comprising an inventive OLED.

Stationary visual display units are, for example, visual display units of computers, televisions, visual display units in printers, kitchen appliances and advertising panels, illuminations and information panels. Mobile visual display units are, for example, visual display units in cellphones, laptops, tablet PCs, digital cameras, mp-3 players, smartphones, vehicles, and destination displays on buses and trains.

The inventive dinuclear metal-carbene complexes can additionally be used in OLEDs with inverse structure. In these inverse OLEDs, the inventive complexes are in turn preferably used in the light-emitting layer. The structure of inverse OLEDs and the materials typically used therein are known to those skilled in the art.

The present invention further provides a white OLED comprising at least one inventive dinuclear metal-carbene complex. In a preferred embodiment, the inventive dinuclear metal-carbene complexes are used as emitter material in the white OLED. Preferred embodiments of the inventive dinuclear metal-carbene complexes have been specified above. In addition to the at least one inventive dinuclear metal-carbene complex, the white OLED may comprise (i) at least one compound of the formula (X). The compound of the formula (X) is preferably used as matrix material. Preferred compounds of the formula (X) have been specified above; and/or (ii) at least one compound of the formula (VII) and/or (IX). The compounds of the formula (VII) and/or (IX) are preferably used as electron transport material. Preferred compounds of the formulae (VII) and (IX) have been specified above.

In order to obtain white light, the OLED must generate light which colors the entire visible range of the spectrum. However, organic emitters normally emit only in a limited portion of the visible spectrum—i.e. are colored. White light can be generated by the combination of different emitters. Typically, red, green and blue emitters are combined. However, the prior art also discloses other methods for formation of white OLEDs, for example the triplet harvesting approach. Suitable structures for white OLEDs or methods for formation of white OLEDs are known to those skilled in the art.

In one embodiment of a white OLED, several dyes are layered one on top of another in the light-emitting layer of an OLED and hence combined (layered device). This can be achieved by mixing all dyes or by direct series connection of different-colored layers. The expression "layered OLED" and suitable embodiments are known to those skilled in the art.

In general, the different layers then have the following thicknesses: anode (2) 500 to 5000 Å (ångström), preferably 1000 to 2000 Å; hole-transporting layer (3) 50 to 1000 Å, preferably 200 to 800 Å, either a light-emitting layer comprising a mixture of different emitters (4): 10 to 1000 Å, preferably 100 to 800 Å, or several light-emitting layers in succession, each individual layer comprising a different emitter (4a, b, c, . . . ): each 10 to 1000 Å, preferably each 50 to 600 Å, electron-transporting layer (5) 50 to 1000 Å, preferably 200 to 800 Å, cathode (6) 200 to 10 000 Å, preferably 300 to 5000 Å.

In a further embodiment of a white OLED, several different-colored OLEDs are stacked one on top of another (stacked device). For the stacking of two OLEDs, what is called a charge generation layer (CG layer) is used. This CG layer may be formed, for example, from one electrically n-doped and one electrically p-doped transport layer. The expression "stacked OLED" and suitable embodiments are known to those skilled in the art.

In general, the different layers then have the following thicknesses: anode (2) 500 to 5000 Å (ångström), preferably 1000 to 2000 Å; first hole-transporting layer (3) 50 to 1000 Å, preferably 200 to 800 Å, first light-emitting layer (4) 10 to 1000 Å, preferably 50 to 600 Å, first electron-transporting layer (5) 50 to 1000 Å, preferably 200 to 800 Å, electrically n-doped layer 50 to 1000 Å, preferably 100 to 800 Å, electrically p-doped layer 50 to 1000 Å, preferably 100 to 800 Å, second hole-transporting layer (3) to 50 to 1000 Å, preferably 200 to 800 Å, second light-emitting layer (4) 10 to 1000 Å, preferably 50 to 600 Å, second electron-transporting layer (5) 50 to 1000 Å, preferably 200 to 800 Å, electrically n-doped layer 50 to 1000 Å, preferably 100 to 800 Å, electrically p-doped layer 50 to 1000 Å, preferably 100 to 800 Å, third hole-transporting layer (3) to 1000 Å, preferably 200 to 800 Å, third light-emitting layer (4) 10 to 1000 Å, preferably 50 to 600 Å, third electron-transporting layer (5) to 50 to 1000 Å, preferably 200 to 800 Å, cathode (6) 200 to 10 000 Å, preferably 300 to 5000 Å.

In further embodiments of this "stacked device concept", it is also possible to stack only two OLEDs or to stack more than three OLEDs.

In a further embodiment of white OLEDs, the two concepts mentioned for white light generation can also be combined. For example, a single-color OLED (for example blue) can be stacked with a multicolor layered OLED (for example red-green). Further combinations of the two concepts are conceivable and known to those skilled in the art.

The inventive dinuclear metal-carbene complexes can be used in any of the layers mentioned above in white OLEDs. In a preferred embodiment, it is used in one or more or all light-emitting layer(s) of the OLED(s), in which case the structure of the invention metal-carbene complex is varied as a function of the use of the complex. Suitable and preferred components for the further layers of the light OLED(s) or materials suitable as matrix material in the light-emitting layer(s) and preferred matrix materials are likewise specified above.

The present invention also relates to an organic electronic component, preferably an organic light-emitting diode (OLED), organic photovoltaic cell (OPV), organic field-effect transistor (OFET) or light-emitting electrochemical cell (LEEC), comprising at least one inventive dinuclear metal-carbene complex.

EXAMPLES

The examples which follow, more particularly the methods, materials, conditions, process parameters, apparatus and the like detailed in the examples, are intended to support the present invention, but not to restrict the scope of the present invention. All experiments are carried out in protective gas atmosphere. The percentages and ratios mentioned in the examples below—unless stated otherwise—are % by weight and weight ratios.

Example 1

1,4-Bis(imidazole)benzene

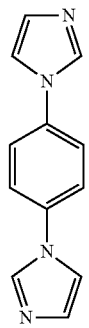 [SMILES: c1cn(-c2ccc(-n3ccnc3)cc2)cn1]

A dried schlenk tube was charged with 1,4-diiodobenzene (4.95 g, 15 mmol), imidazole (3.57 g, 52.5 mmol), potassium hydroxide (2.95 g, 52.5 mmol) and copper(I) oxide (0.43 g, 3 mmol) under an argon atmosphere and dry DMSO was added through a septum after an additional degassing phase of the solids. The suspension was stirred for 48 hours at 130° C. After cooling to room temperature the reaction mixture was poured into a water/ethyl acetate solution (1:3). Solids were filtered off and the phases separated. The aqueous phase was extracted with ethyl acetate (6×60 mL), organic phases were combined, washed with brine (50 mL) and dried over sodium sulfate. After concentration under reduced pressure the solid product was precipitated and washed with diethyl ether. Collecting the solid and drying under vacuum yielded the off-white product (1.55 g, 49.3%).

$^1$H-NMR (CDCl$_3$, 300.13 MHz): δ=7.87 (s, 2H, NCHN), 7.51 (s, 4H, CH$_{arom.}$), 7.30 (t, J=1.3 Hz, 2H, CH), 7.23 (s, 2H, CH) ppm. $^{13}$C-NMR (CDCl$_3$, 75.475 MHz): δ=136.4 (NCHN), 135.5 (C$_i$), 130.9 (CH), 122.8 (CH$_{arom.}$), 118.1 (CH) ppm. M.p. 208-210° C. Anal. Calc. for Cl$_{12}$H$_{10}$N$_4$ (210.24 g mol$^{-1}$): C, 68.56; H, 4.79; N, 26.65. Found: C, 68.27; H, 4.98; N, 26.67%.

1,4-Bis(3-methylimidazolium)benzene iodide

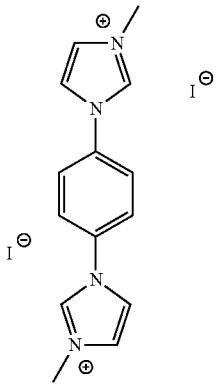

A sealed tube is charged with 1,4-bis(imidazole)benzene (1.05 g, 5 mmol) and iodomethane (1.9 mL, 30 mmol). After addition of 8 mL THF the tube is sealed and the reaction mixture stirred for 72 h at 100° C. The generated solid is filtered off and washed with small portions of tetrahydrofuran and diethyl ether. After drying under vacuum an off-white solid is yielded (2.42 g, 98%). $^1$H-NMR (d$_6$-DMSO, 300.13 MHz): δ=9.90 (s, 2H, NCHN), 8.39 (s, 2H, CH), 8.10 (s, 4H, CH$_{arom.}$), 8.00 (s, 2H, CH), 3.98 (s, 6H, CH$_3$) ppm.
$^{13}$C-NMR (d$_6$-DMSO, 75.475 MHz): δ=136.3 (NCHN), 135.2 (C$_i$), 124.6 (CH), 123.3 (CH$_{arom.}$), 120.9 (CH), 36.3 (CH$_3$) ppm. Dec. >ca. 300° C. Anal. Calc. for Cl$_4$H$_{16}$I$_2$N$_4$ (494.12 g mol$^{-1}$): C, 34.03; H, 3.26; N, 11.34. Found: C, 33.94; H, 3.16; N, 11.33%.

EM1 (D-1)

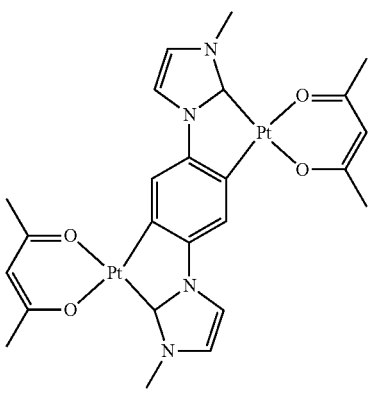

A dried and argon flushed schlenk tube was charged with 1,4-bis(3-methylimidazolium)benzene iodide (0.40 g, 0.8 mmol) and silver(I) oxide (0.20 g, 0.88 mmol). After addition of 20 mL dry 1,4-dioxane the reaction mixture was stirred under argon in the dark at room temperature for 48 h. Dichloro(1,5-cyclooctadiene)platinum(II) (0.75 g, 2 mmol) and 10 mL 2-butanone were added and the mixture was heated to 115° C. and stirred for another 54 h. Afterwards all volatiles were removed under reduced pressure and potassium tert-butanolate (0.72 g, 6.4 mmol), acetylacetone (0.66 mL, 6.4 mmol) and 25 mL dry DMF were added under argon. After stirring for 28 h at room temperature and 14 h at 100° C. all volatiles were again removed under reduced pressure leaving the crude product, which was washed with water and purified by flash chromatography with methylene chloride/acetone 5/1. The product containing fraction was finally recrystallized from methylene chloride/tetrahydrofuran 1/1 solution and dried under vacuum yielding a light-yellow solid (0.03 g, 5%). $^1$H-NMR (d$_6$-DMSO, 300.13 MHz): δ=7.77 (d, J=2.0 Hz, 2H, NCH), 7.32 (d, J=2.0 Hz, 2H, NCH), 7.21 (s, 2H, CH$_{arom.}$), 5.57 (s, 2H, OCCH), 3.98 (s, 6H, NCH$_3$), 2.05 (s, 6H, CCH$_3$), 1.92 (s, 6H, CCH$_3$) ppm. $^{13}$C-NMR (d$_6$-DMSO, 150.927 MHz): δ=184.1 (CO), 146.6 (NCN), 141.8 (PtC), 121.6 (NCH), 118.8 (NC), 114.9 (NCH), 113.4 (CH$_{arom.}$), 101.7 (CH), 34.2 (NCH$_3$), 27.7 (CCH$_3$) ppm. Dec. >310° C. Anal. Calc. for C$_{24}$H$_{26}$N$_4$O$_4$Pt$_2$ (824.66 g mol$^{-1}$): C, 34.95; H, 3.18; N, 6.78. Found: C, 34.69; H, 3.15; N, 6.57%.

Example 2

EM2 (D-2)

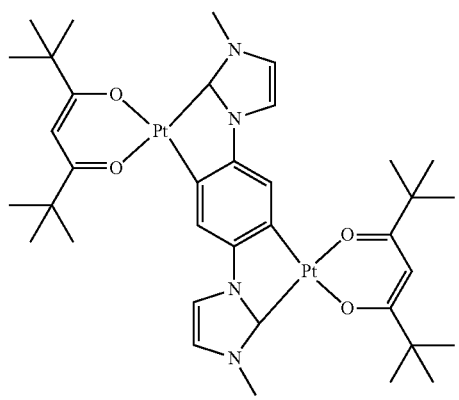

A dried and argon flushed schlenk tube was charged with 1,4-bis(3-methylimidazolium)benzene iodide (0.99 g, 2 mmol) and silver(I) oxide (0.70 g, 3 mmol). After addition of 30 mL dry 1,4-dioxane the reaction mixture was stirred under argon in the dark at room temperature for 72 h. Dichloro(1,5-cyclooctadiene)platinum(II) (1.87 g, 5 mmol) and 15 mL 2-butanone were added and the mixture was heated to 115° C. and stirred for another 96 h. Afterwards all volatiles were removed under reduced pressure and potassium tert-butanolate (1.79 g, 16 mmol), 2,2,6,6-tetramethyl-3,5-heptanedione (2.95 g, 16 mmol) and 30 mL dry DMF were added under argon. After stirring for 3 days at room temperature and 24 h at 100° C. all volatiles were again removed under reduced pressure leaving the crude product, which was washed with water and purified by flash chromatography with methylene chloride. The product containing fraction was finally washed with diethyl ether to remove traces of the dione and dried under vacuum yielding a light-yellow solid (0.33 g, 16%). $^1$H-NMR (CDCl$_3$, 600.16 MHz): δ=7.44 (pseudo-t, J$_{H,Pt}$=27.5 Hz, 2H, CH$_{arom.}$), 7.20 (d, J=2.0 Hz, 2H, NCH), 6.77 (d, J=2.0 Hz, 2H, NCH), 5.81 (s, 2H, OCCH), 4.09 (s, 6H, NCH$_3$), 1.33 (s, 18H, CCH$_3$), 1.21 (s, 18H, CCH$_3$) ppm. $^{13}$C-NMR (CDCl$_3$, 150.91 MHz): δ=194.4 (CO), 193.8 (CO), 149.3 (NCN), 142.5 (PtC), 119.8

(NCH), 119.1 (NC), 114.3 (NCH), 113.5 ($CH_{arom.}$), 92.8 (OCCH), 42.0 ($CCH_3$), 41.4 ($CCH_3$), 35.1 ($NCH_3$), 28.8 ($CH_3$), 28.7 ($CH_3$), ppm. $^{195}$Pt-NMR ($CDCl_3$, 64.52 MHz): δ=−3402.7 (d, J=52.0 Hz) ppm. Dec. >275° C. Anal. Calc. for $C_{36}H_{50}N_4O_4Pt_2$ (992.98 g mol$^{-1}$): C, 43.55; H, 5.08; N, 5.64. Found: C, 43.58; H, 5.31; N, 5.49%.

Photoluminescence (2% in PMMA matrix):

$λ_{max}$=488 nm, CIE: (0.23; 0.54); QY=82%.

Example 3

EM3 (D-3)

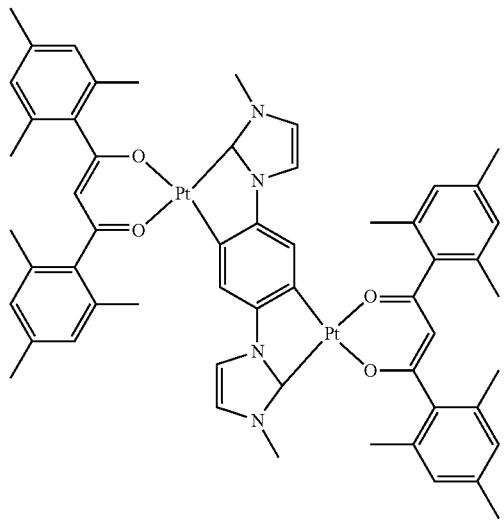

A dried and argon flushed schlenk tube was charged with 1,4-bis(3-methylimidazolium)benzene iodide (0.40 g, 0.8 mmol) and silver(I) oxide (0.19 g, 0.8 mmol). After addition of 20 mL dry 1,4-dioxane the reaction mixture was stirred under argon in the dark at room temperature for 48 h. Dichloro(1,5-cyclooctadiene)platinum(II) (0.75 g, 2 mmol) and 10 mL 2-butanone were added and the mixture was heated to 115° C. and stirred for another 48 h. Afterwards all volatiles were removed under reduced pressure and potassium tert-butanolate (0.72 g, 6.4 mmol), dimesitoylmethane (1.97 g, 6.4 mmol) and 20 mL dry DMF were added under argon. After stirring for 64 h at room temperature and 7 h at 100° C. all volatiles were again removed under reduced pressure leaving the crude product, which was washed with water and purified by flash chromatography with methylene chloride/acetone. Drying under vacuum yielding a light-yellow solid (0.21 g, 21%). $^1$H-NMR ($CDCl_3$, 600.16 MHz): δ=7.24 (s, 2H, $CH_{arom.}$), 7.14 (d, J=2.0 Hz, 2H, NCH), 6.86 (s, 4H, $CH_{arom.}$), 6.82 (s, 4H, $CH_{arom.}$), 6.66 (d, J=2.0 Hz, 2H, NCH), 5.64 (s, 2H, OCCH), 3.87 (s, 6H, $NCH_3$), 2.37 (s, 12H, $CCH_3$), 2.31 (s, 12H, $CCH_3$), 2.30 (s, 6H, $CCH_3$), 2.28 (s, 6H, $CCH_3$) ppm. $^{13}$C-NMR ($CDCl_3$, 150.91 MHz): δ=184.6 (CO), 183.9 (CO), 147.7 (NCN), 142.7 (PtC), 139.9 ($C_i$), 139.4 ($C_i$), 137.4 ($C_i$), 137.2 ($C_i$), 134.3 ($C_i$), 133.7 ($C_i$), 128.2 ($CH_{arom.}$), 128.0 ($CH_{arom.}$), 120.0 (NCH), 118.5 (NC), 114.8 (NCH), 113.7 ($CH_{arom.}$), 107.2 (OCCH), 34.8 ($NCH_3$), 21.12 ($CH_3$), 21.08 ($CH_3$), 20.1 ($CH_3$), 19.5 ($CH_3$) ppm. $^{195}$Pt-NMR ($CDCl_3$, 64.52 MHz): δ=−3354.8 (s) ppm. M.p. 240-242° C. Anal. Calc. for $C_{56}H_{58}N_4O_4Pt_2$ (1241.26 g mol$^{-1}$): C, 54.19; H, 4.71; N, 4.51. Found: C, 54.13; H, 4.87; N, 4.35%.

Photoluminescence (2% in PMMA matrix):

$λ_{max}$=489 nm, CIE: (0.26; 0.54); QY=76%

Example 4

2,2'-(1,4-phenylene)bisimidazo[1,5-a]pyridinium chloride

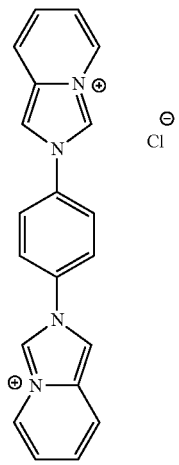

Pyridine-2-aldehyde (4.28 g, 40 mmol), 4-phenylenediamine dihydrochloride (3.66 g, 20 mmol) and 37 wt % formaldehyde solution (4.5 mL, 60 mmol) were dissolved in 50 mL ethanol and stirred at room temperature over night. The precipitated solid was filtered off and washed with small portions of ethanol and diethyl ether. Drying under vacuum yielded the off-white product (5.81 g, 76%). $^1$H-NMR ($d_6$-DMSO, 300.13 MHz): δ=10.81 (d, J=5.7 Hz, 2H, NCHN), 8.95 (s, 2H, CHN), 8.71 (d, J=6.9 Hz, 2H, CH), 8.35 (s, 4H, $CH_{arom.}$), 7.98 (d, J=9.2 Hz, 2H, CH), 7.35 (m, 4H, CH) ppm. $^{13}$C-NMR ($d_6$-DMSO, 75.475 MHz): δ=136.2 ($C_i$), 129.8 ($C_i$), 126.4 (CH), 125.5 (CH), 124.7 ($CH_{arom.}$), 124.2 (CH), 118.5 (CH), 118.4 (CH), 112.3 (CH) ppm. M.p. >325° C.

EM4 (F-1)

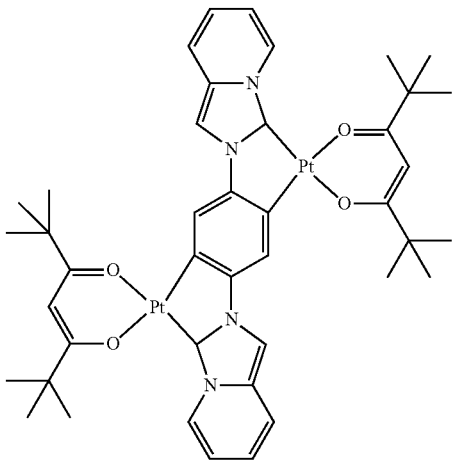

A dried and argon flushed schlenk tube was charged with 2,2'-(1,4-phenylene)bisimidazo[1,5-a]pyridinium chloride (0.31 g, 0.8 mmol) and silver(I) oxide (0.28 g, 1.5 mmol). After addition of 20 mL dry 1,4-dioxane the reaction mixture was stirred in the dark under argon at room temperature for 72 h. Dichloro(1,5-cyclooctadiene)platinum(II) (0.75 g, 2 mmol) and 10 mL 2-butanone were added and the mixture was heated to 115° C. and stirred for another 48 h. Afterwards all volatiles were removed under reduced pressure and potassium tert-butanolate (0.72 g, 6.4 mmol), 2,2,6,6-tetramethyl-3,5-heptanedione (1.34 mL, 6.4 mmol) and 20 mL dry DMF were added under argon. After stirring for 64 h at room temperature and 7 h at 100° C. all volatiles were again removed under reduced pressure leaving the crude product, which was washed with water and purified by flash chromatography with methylene chloride. Drying under vacuum yielding a light-yellow solid (0.04 g, 5%). $^1$H-NMR (CDCl$_3$, 600.16 MHz): δ=9.20 (d, J=6.7 Hz, 2H, CH$_{arom.}$), 7.51 (s, 2H, CH$_{arom.}$), 7.43 (s, 2H, CH$_{arom.}$), 7.28 (s, 2H, CH$_{arom.}$), 6.76 (dd, J$_1$=6.1 Hz, J$_2$=9.4 Hz, 2H, CH$_{arom.}$), 6.51 (t, J=6.4 Hz, 2H, CH$_{arom.}$), 5.88 (s, 2H, CH), 1.39 (s, 18H, CH$_3$), 1.30 (s, 18H, CH$_3$) ppm.
$^{13}$C-NMR (CDCl$_3$, 150.91 MHz): δ=194.5 (CO), 194.0 (CO), 143.5 (PtC), 140.8 (C$_i$), 129.3 (C$_i$), 126.2 (CH$_{arom.}$), 121.2 (CH$_{arom.}$), 117.8 (CH$_{arom.}$), 115.2 (CH$_{arom.}$), 112.8 (CH$_{arom.}$), 103.9 (NCH), 93.0 (OCCH), 42.0 (CCH$_3$), 41.5 (CCH$_3$), 28.7 (CH$_3$) ppm. Dec. >290° C. Anal. Calc. for C$_{42}$H$_{50}$N$_4$O$_4$Pt$_2$ (1065.04 g mol$^{-1}$): C, 47.37; H, 4.73; N, 5.26. Found: C, 47.23; H, 4.76; N, 4.91%.
Photoluminescence (2% in PMMA matrix):
λ$_{max}$=585 nm, CIE: (0.59; 0.41)

Example 5

1,3-Bis(imidazole)benzene

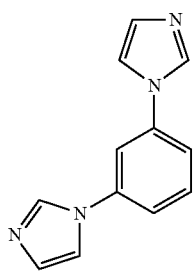 [SMILES: c1cc(-n2ccnc2)cc(-n2ccnc2)c1]

A dried schlenk tube was charged with 1,3-diiodobenzene (3.30 g, 10 mmol), imidazole (2.04 g, 30 mmol), potassium hydroxide (2.24 g, 40 mmol) and copper(I) oxide (0.29 g, 2 mmol) under an argon atmosphere and dry DMSO was added through a septum after an additional degassing phase of the solids. The suspension was stirred for 48 hours at 120° C. After cooling to room temperature the reaction mixture was poured into a water/ethyl acetate solution (1:3). Solids were filtered off and the phases separated. The aqueous phase was extracted with ethyl acetate (3×50 mL), organic phases were combined, washed with brine (50 mL) and dried over magnesium sulfate. The crude product was purified by flash chromatography with ethyl acetate yielding a pale crystalline solid (1.29 g, 61.3%). $^1$H-NMR (CDCl$_3$, 300.13 MHz): δ=7.93 (s, 2H, NCHN), 7.62 (t, J=7.9 Hz, 1H, CH$_{arom.}$), 7.43 (s, 2H), 7.41 (s, 1H, CH$_{arom.}$), 7.33 (s, 2H), 7.24 (s, 2H) ppm. $^{13}$C-NMR (CDCl$_3$, 75.475 MHz): δ=138.7 (C$_i$), 135.5 (NCHN), 131.5 (CH$_{arom.}$), 131.0 (CH$_{arom.}$), 120.2 (CH$_{arom.}$), 118.1 (CH$_{arom.}$), 114.6 (CH$_{arom.}$) ppm. M.p. 129-131° C. Anal. Calc. for C$_{12}$H$_{10}$N$_4$ (210.24 g mol$^{-1}$): C, 68.56; H, 4.79; N, 26.65. Found: C, 68.35; H, 4.74; N, 26.75%.

1,3-Bis(3-methylimidazolium)benzene iodide

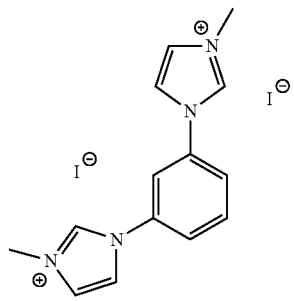

A sealed tube was charged with 1,3-bis(imidazole)benzene (0.42 g, 2 mmol) and iodomethane (1.2 mL, 8 mmol). After addition of 5 mL THF the tube was sealed and the reaction mixture stirred for 48 h at 100° C. The generated solid was filtered off and washed with small portions of tetrahydrofuran and diethyl ether. After drying under vacuum an off-white solid was yielded (0.97 g, 98%). $^1$H-NMR (d$_6$-DMSO, 600.16 MHz): δ=9.90 (s, 2H, NCHN), 8.38 (s, 2H, CH), 8.31 (s, 1H, CH$_{arom.}$), 8.03 (s, 2H, CH), 8.00 (m, 3H), 3.99 (s, 6H, CH$_3$) ppm. $^{13}$C-NMR (d$_6$-DMSO, 150.91 MHz): δ=136.4 (NCHN), 135.8 (C$_i$), 132.1 (CH$_{arom.}$), 124.8 (CH), 122.6 (CH$_{arom.}$), 121.0 (CH), 115.7 (CH$_{arom.}$), 36.3 (CH$_3$) ppm. M.p. 266-269° C. Anal. Calc. for C$_{14}$H$_{16}$I$_2$N$_4$ (494.12 g mol$^{-1}$): C, 34.03; H, 3.26; N, 11.34. Found: C, 33.88; H, 3.19; N, 11.32%.

EM5 (E-1)

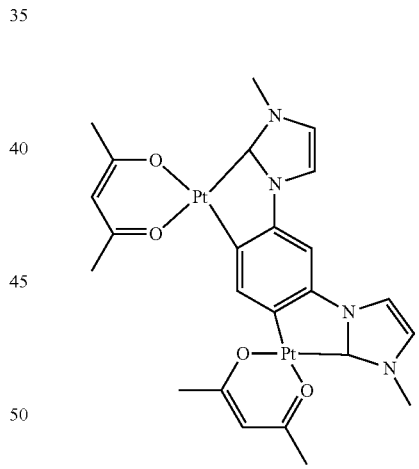

A dried and argon flushed schlenk tube was charged with 1,3-bis(3-methylimidazolium)benzene iodide (0.40 g, 0.8 mmol) and silver(I) oxide (0.19 g, 0.8 mmol). After addition of 20 mL dry 1,4-dioxane the reaction mixture was stirred under argon in the dark at room temperature for 48 h. Dichloro(1,5-cyclooctadiene)platinum(II) (0.75 g, 2 mmol) and 10 mL 2-butanone were added and the mixture was heated to 115° C. and stirred for another 48 h. Afterwards all volatiles were removed under reduced pressure and potassium tert-butanolate (0.72 g, 6.4 mmol), acetylacetone (0.66 mL, 6.4 mmol) and 25 mL dry DMF were added under argon. After stirring for 60 h at room temperature and 16 h at 100° C. all volatiles were again removed under reduced pressure leaving the crude product, which was washed with water and purified by flash chromatography with methylene chloride/acetone. Drying under vacuum yielding an off-white solid (0.06 g, 7%).

$^1$H-NMR (d$_6$-DMSO, 600.16 MHz): δ=7.82 (s, 1H, CH$_{arom.}$), 7.66 (d, J=2.0 Hz, 2H, NCH), 7.32 (d, J=2.0 Hz, 2H, NCH), 7.25 (s, 1H, CH$_{arom.}$), 5.56 (s, 2H, OCCH), 3.98 (s, 6H, NCH$_3$), 1.99 (s, 6H, CCH$_3$), 1.92 (s, 6H, CCH$_3$) ppm. $^{13}$C-NMR (d$_6$-DMSO, 150.91 MHz): δ=184.6 (CO), 183.8 (CO), 147.4 (NCN), 142.3 (PtC), 134.7 (CH$_{arom.}$), 121.9 (NCH), 118.9 (C$_i$), 114.4 (NCH), 101.6 (OCCH), 96.2 (CH$_{arom.}$), 34.1 (NCH$_3$), 27.8 (CH$_3$), 27.4 (CH$_3$) ppm. $^{195}$Pt-NMR (d$_6$-DMSO, 64.52 MHz): δ=−3416.3 ppm. M.p. >320° C. Anal. Calc. for C$_{24}$H$_{26}$N$_4$O$_4$Pt$_2$ (824.66 g mol$^{-1}$): C, 34.96; H, 3.18; N, 6.79. Found: C, 34.58; H, 3.02; N, 6.42%.

Application Example 1

The ITO substrate used as the anode is cleaned first with commercial detergents for LCD production (Deconex® 20NS, and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Thereafter, the organic materials specified below are applied by vapor deposition to the cleaned substrate at about $10^{-7}$-$10^{-9}$ mbar at a rate of approx. 0.5-5 nm/min. The hole

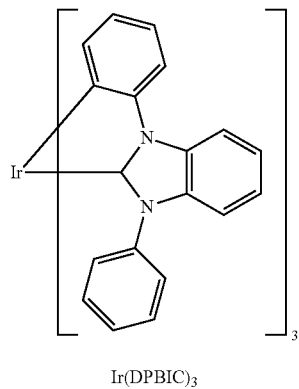

Ir(DPBIC)$_3$ conductor and exciton blocker applied to the substrate is (for preparation of Ir(DPBIC)$_3$ see Ir complex (7) in the application WO2005/19373) with a thickness of 20 nm, of which the first 10 nm are doped with MoO$_x$ to improve the conductivity.

Subsequently, a mixture of emitter Em2 (30% by wt.), Ir(DPBIC)$_3$ (20% by wt.), and compound Ma2

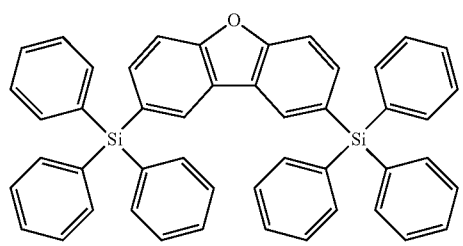

(50% by wt.; compound "4g" in WO2009/003898) is applied by vapor deposition with a thickness of 40 nm, the latter compounds functioning as matrix materials.

Subsequently, the material Ma2 is applied by vapor deposition with a thickness of 5 nm as a hole blocker. Next, as an electron transporting layer, a mixture of Cs$_2$CO$_3$ (5% by wt.) and BCP (2,9-dimethyl-4,7-diphenyl-1,10-phenanthroline; 95% by wt.) is applied by vapor deposition and finally a 100 nm-thick Al electrode. All components are adhesive-bonded to a glass lid in an inert nitrogen atmosphere.

Application Example 2

Application Example 1 is repeated, except that

Ma1

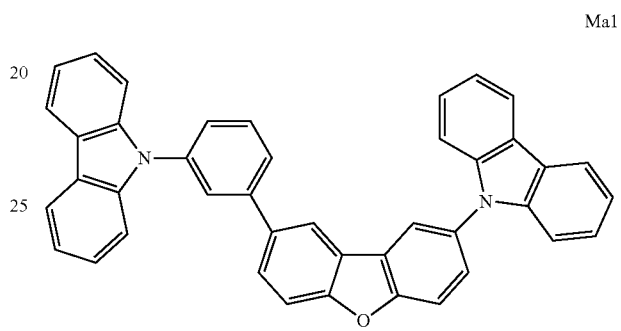

(WO2009/008100) is used instead of compound Ma2 in the emitting and hole blocking layer, a mixture of

T1

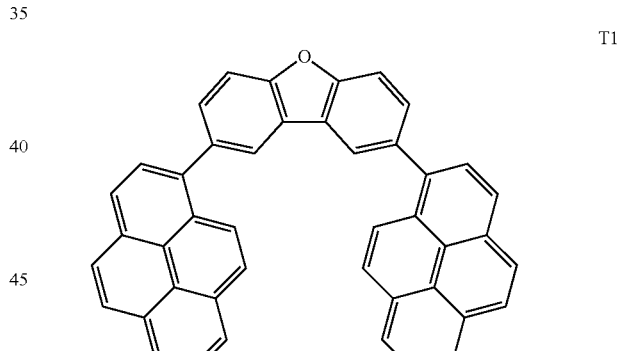

(50% by wt.; WO2011/157779) and

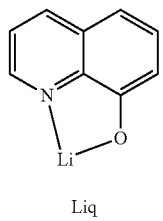

Liq (50% by wt.) constitutes the 20 nm thick electron transport layer and a 2 nm KF functions as hole injection layer.

To characterize the OLED, electroluminescence spectra are recorded at different currents and voltages. In addition, the current-voltage characteristic is measured in combination with the light output emitted. The light output can be converted to photometric parameters by calibration with a photometer.

Application Example 1

$\lambda_{max}$=534 nm, CIE: (0.27; 0.57); U=5.2 V; EQE (external quantum efficiency is # of generated photons escaped from a substance or a device/# of electrons flowing through it)=6.6%

Application Example 2

$\lambda_{max}$=533 nm, CIE: (0.27; 0.57); U=3.1 V; EQE=13.4%
Dependency of CIE Color Coordinates from Doping Concentration Devices according to application example 1 were fabricated with varying emitter concentrations in the emissive layer:

HIL Plexcore AJ20-1000–10 nm Ir(DPBIC)$_3$:MoO$_x$ (90:10)–10 nm Ir(DPBIC)$_3$–40 nm Em2: Ma2 (X:(100-X))–5 nm Ma2–25 nm BCP:Cs$_2$CO$_3$ (95:5)–100 nm Al;

By varying the doping concentration of Em2 from 5% to 30% the influence on the color coordinates of the emitted light was determined.

| Amount of X in EML [%] | 5 | 10 | 20 | 30 |
|---|---|---|---|---|
| CIE (x;y) | 0.27;0.54 | 0.27;0.55 | 0.27;0.56 | 0.27;0.56 |

As these results clearly demonstrate there is only a minor shift in color coordinates when significantly altering the doping concentration in a range from 5% to 30%. This low concentration dependency is especially important for reproducibility in mass production.

The invention claimed is:
1. A metal-carbene complex of formula

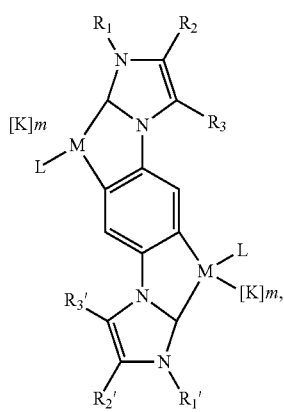

(I)

or

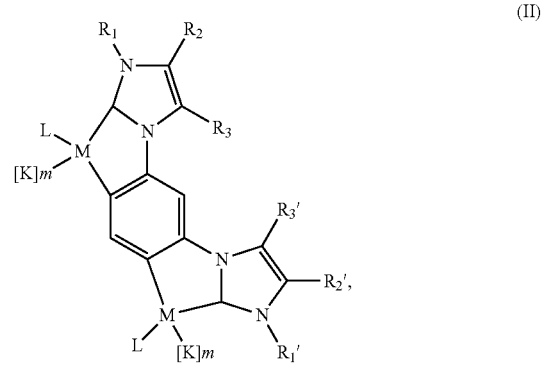

(II)

wherein
M is Pd or Pt,
m is an integer selected from 0 or 1,
R$_1$ and R$_1$' are each independently a linear or branched alkyl radical optionally interrupted by a heteroatom, optionally bearing a functional group and having 1 to 20 carbon atoms, substituted or unsubstituted cycloalkyl radical optionally interrupted by a heteroatom, optionally bearing a functional group and having 3 to 20 carbon atoms, substituted or unsubstituted aryl radical, optionally bearing a functional group and having 6 to 30 carbon atoms, or substituted or unsubstituted heteroaryl radical optionally interrupted by a heteroatom, optionally bearing a functional group and having a total of 5 to 18 carbon atoms and/or heteroatoms;
R$_2$, R$_2$', R$_3$ and R$_3$' are each independently hydrogen, a linear or branched alkyl radical optionally interrupted by a heteroatom, optionally bearing a functional group and having 1 to 20 carbon atoms, substituted or unsubstituted cycloalkyl radical optionally interrupted by a heteroatom, optionally bearing a functional group and having 3 to 20 carbon atoms, substituted or unsubstituted aryl radical optionally interrupted by a heteroatom, optionally bearing a functional group and having 6 to 30 carbon atoms, substituted or unsubstituted heteroaryl radical optionally interrupted by a heteroatom, optionally bearing a functional group and having a total of 5 to 18 carbon atoms and/or heteroatoms, or a group with donor or acceptor action, or
R$_1$ and R$_2$ and/or R$_1$' and R$_2$' together with the atoms to which they are bonded form an optionally substituted, saturated or unsaturated or aromatic ring optionally interrupted by a further heteroatom and having a total of 5 to 18 carbon atoms and/or heteroatoms, and may optionally be fused to a further optionally substituted saturated or unsaturated or aromatic ring optionally interrupted by a further heteroatom and having a total of 5 to 18 carbon atoms and/or heteroatoms;
K is a neutral monodentate ligand, and
L is a monoanionic ligand, which can be mono- or bidentate.
2. The metal-carbene complex according to claim 1, wherein
m is 0; and
L is a monoanionic bidentate ligand.
3. The metal-carbene complex according to claim 2, wherein
L is selected from the group consisting of picolinato, salicylato, 8-hydroxyquinolato, and ligands of formula (A)

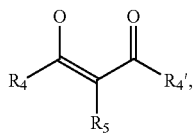
(A)

wherein
R$_4$ and R$_4$' are in each case independently a linear or branched alkyl radical having 1 to 6 carbons atoms optionally bearing a functional group; substituted or unsubstituted cycloalkyl radical having 3 to 20 carbon atoms, substituted or unsubstituted aryl radical having 6 to 20 carbon atoms; or substituted or unsubstituted heteroaryl radical having a total of 5 to 18 carbon atoms and/or heteroatoms, and R$_5$ is hydrogen, a linear or branched alkyl radical having 1 to 6 carbon atoms, or a substituted or unsubstituted aryl radical having 6 to 20 carbon atoms.

4. An organic electronic device comprising a metal-carbene complex according to claim 1.

5. An apparatus selected from the group consisting of stationary visual display units, mobile visual display units; illumination units, keyboards, items of clothing, furniture, and wallpaper, the apparatus comprising the organic electronic device according to claim 4.

6. The organic electronic device according to claim 4, wherein the organic electronic component is selected from the group consisting of organic light-emitting diodes (OLEDs), organic photovoltaic cells (OPVs), organic field-effect transistors (OFETs) and light-emitting electrochemical cells (LEECs).

7. The organic electronic component according to claim 6, wherein the organic electronic component is an OLED comprising a light-emitting layer comprising the metal-carbene complex.

8. A light-emitting layer comprising a metal-carbene complex according to claim 1.

9. The light-emitting layer according to claim 8, comprising the metal-carbene complex and a host material.

10. The metal-carbene complex according to claim 1, wherein the complex is suitable for electrophotographic photoreceptors, photoelectric converters, organic solar cells (organic photovoltaics), switching elements, organic light emitting field effect transistors (OLEFETs), image sensors, dye lasers and organic light emitting devices.

11. The metal-carbene complex according to claim 10, wherein the metal-carbene complex is configured in organic light emitting devices as charge transport material, charge blocker material, or matrix material.

12. A metal-carbene complex of formula

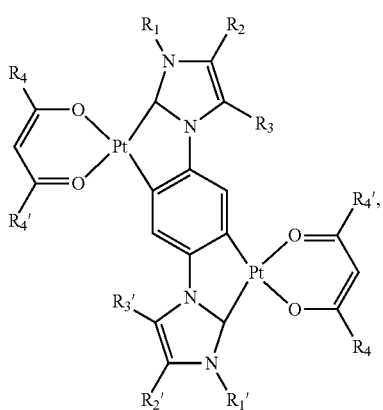
(III)

or

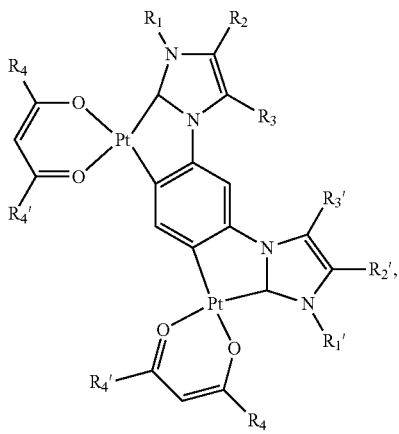
(IV)

wherein
R$_1$ and R$_1$' are each independently a linear or branched alkyl radical having 1 to 6 carbon atoms, substituted or unsubstituted cycloalkyl radical having 3 to 20 carbon atoms, substituted or unsubstituted aryl radical having 6 to 30 carbon atoms, or substituted or unsubstituted heteroaryl radical having a total of 5 to 18 carbon atoms and/or heteroatoms, R$_2$, R$_2$', R$_3$ and R$_3$' are each independently hydrogen, a linear or branched alkyl radical having 1 to 6 carbon atoms, substituted or unsubstituted cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, or a group with donor or acceptor action selected from halogen radicals; or R$_1$ and R$_2$ and/or R$_1$' and R$_2$' form, together with the atoms to which they are bonded, an optionally substituted unsaturated, saturated or aromatic ring which is optionally interrupted by a further heteroatom, has a total of 5 to 18 carbon atoms and/or heteroatoms and may optionally be fused to a further optionally substituted saturated or unsaturated or aromatic ring optionally interrupted by a further heteroatom and having a total of 5 to 18 carbon atoms and/or heteroatoms, and R$_4$ and R$_4$' are in each case independently a linear or branched alkyl radical having 1 to 6 carbons atoms; substituted or unsubstituted aryl radical having 6 to 20 carbon atoms; or substituted or unsubstituted heteroaryl radical having a total of 5 to 18 carbon atoms and/or heteroatoms.

13. The metal-carbene complex according to claim 12, wherein
R$_1$ is a linear or branched alkyl radical having 1 to 6 carbon atoms, substituted or unsubstituted cycloalkyl radical having 3 to 12 carbon atoms, or substituted or unsubstituted aryl radical having 6 to 15 carbon atoms, R$_2$ and R$_3$ are each independently hydrogen, a linear or branched alkyl radical having 1 to 6 carbon atoms, substituted or unsubstituted aryl radical having 6 to 18 carbon atoms, or a group with donor or acceptor action selected from halogen radicals; or R$_1$ and R$_2$ form, together with the atoms to which they are bonded, an optionally substituted unsaturated, saturated or aromatic ring which is optionally interrupted by a further heteroatom, has a total of 5 to 18 carbon atoms and/or heteroatoms, and $R_4$ and $R_4'$ are in each case independently a linear or branched alkyl radical having 1 to 6 carbons atoms; or a substituted or unsubstituted aryl radical having 6 to 15 carbon atoms.

14. A process for preparing the metal-carbene complex according to claim 1, comprising contacting a compound comprising M with a compound of formula

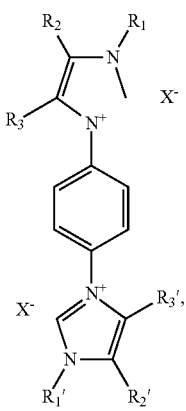

(V)

or

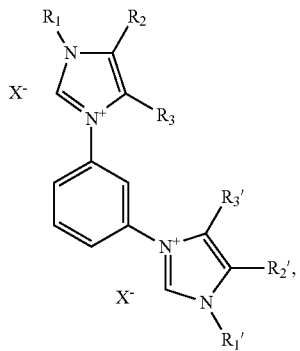

(VI)

wherein $R_1$, $R_1'$, $R_2$, $R_2'$, $R_3'$ and $R_3$ are each as defined according to claim 1 for the compounds of formula (I) or (II), and X is F, Cl, Br, I, $PF_6$, or $BF_4$.

* * * * *